(12) United States Patent
Hunter et al.

(10) Patent No.: US 7,660,623 B2
(45) Date of Patent: Feb. 9, 2010

(54) SIX DEGREE OF FREEDOM ALIGNMENT DISPLAY FOR MEDICAL PROCEDURES

(75) Inventors: Mark Hunter, Broomfield, CO (US); Greg Rutz, Boulder, CO (US); Torsten Lyon, Broomfield, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 1195 days.

(21) Appl. No.: 10/354,562

(22) Filed: Jan. 30, 2003

(65) Prior Publication Data

US 2004/0152970 A1 Aug. 5, 2004

(51) Int. Cl.
 *A61B 5/05* (2006.01)
 *G06T 15/00* (2006.01)
(52) U.S. Cl. ...................................... 600/424; 345/418
(58) Field of Classification Search ................ 600/424, 600/407, 473, 476, 429, 159; 606/130, 159; 382/128; 345/418, 157–158, 90, 60, 2, 1.1, 345/10
See application file for complete search history.

(56) References Cited

U.S. PATENT DOCUMENTS

| | | |
|---|---|---|
| 1,576,781 A | 3/1926 | Phillips |
| 1,735,726 A | 11/1929 | Bornhardt |
| 2,407,845 A | 9/1946 | Nemeyer |
| 2,650,588 A | 9/1953 | Drew |
| 2,697,433 A | 12/1954 | Sehnder |
| 3,016,899 A | 1/1962 | Stenvall |
| 3,017,887 A | 1/1962 | Heyer |
| 3,061,936 A | 11/1962 | Dobbeleer |
| 3,073,310 A | 1/1963 | Mocarski |
| 3,109,588 A | 11/1963 | Polhemus et al. |
| 3,294,083 A | 12/1966 | Alderson |
| 3,367,326 A | 2/1968 | Frazier |
| 3,439,256 A | 4/1969 | Kähne et al. |
| 3,577,160 A | 5/1971 | White |
| 3,614,950 A | 10/1971 | Rabey |
| 3,644,825 A | 2/1972 | Davis, Jr. et al. |
| 3,674,014 A | 7/1972 | Tillander |
| 3,702,935 A | 11/1972 | Carey et al. |

(Continued)

FOREIGN PATENT DOCUMENTS

CA 964149 3/1975

(Continued)

OTHER PUBLICATIONS

Adams et al., Computer-Assisted Surgery, IEEE Computer Graphics & Applications, pp. 43-51, (May 1990).

(Continued)

*Primary Examiner*—Eric F Winakur
*Assistant Examiner*—Lawrence N Laryea
(74) *Attorney, Agent, or Firm*—Harness, Dickey

(57) ABSTRACT

A display and navigation system for use in guiding a medical device to a target in a patient includes a tracking sensor, a tracking device and display. The tracking sensor is associated with the medical device and is used to track the medical device. The tracking device tracks the medical device with the tracking sensor. The display includes indicia illustrating at least five degree of freedom information and indicia of the medical device in relation to the five degree of freedom information.

52 Claims, 13 Drawing Sheets

U.S. PATENT DOCUMENTS

| | | | |
|---|---|---|---|
| 3,704,707 | A | 12/1972 | Halloran |
| 3,821,469 | A | 6/1974 | Whetstone et al. |
| 3,868,565 | A | 2/1975 | Kuipers |
| 3,941,127 | A | 3/1976 | Froning |
| 3,983,474 | A | 9/1976 | Kuipers |
| 4,017,858 | A | 4/1977 | Kuipers |
| 4,037,592 | A | 7/1977 | Kronner |
| 4,052,620 | A | 10/1977 | Brunnett |
| 4,054,881 | A | 10/1977 | Raab |
| 4,117,337 | A | 9/1978 | Staats |
| 4,173,228 | A | 11/1979 | Van Steenwyk et al. |
| 4,182,312 | A | 1/1980 | Mushabac |
| 4,202,349 | A | 5/1980 | Jones |
| 4,228,799 | A | 10/1980 | Anichkov et al. |
| 4,256,112 | A | 3/1981 | Kopf et al. |
| 4,262,306 | A | 4/1981 | Renner |
| 4,287,809 | A | 9/1981 | Egli et al. |
| 4,298,874 | A | 11/1981 | Kuipers |
| 4,314,251 | A | 2/1982 | Raab |
| 4,317,078 | A | 2/1982 | Weed et al. |
| 4,319,136 | A | 3/1982 | Jinkins |
| 4,328,548 | A | 5/1982 | Crow et al. |
| 4,328,813 | A | 5/1982 | Ray |
| 4,339,953 | A | 7/1982 | Iwasaki |
| 4,341,220 | A | 7/1982 | Perry |
| 4,346,384 | A | 8/1982 | Raab |
| 4,358,856 | A | 11/1982 | Stivender et al. |
| 4,368,536 | A | 1/1983 | Pfeiler |
| 4,396,885 | A | 8/1983 | Constant |
| 4,396,945 | A | 8/1983 | DiMatteo et al. |
| 4,403,321 | A | 9/1983 | DiMarco |
| 4,418,422 | A | 11/1983 | Richter et al. |
| 4,419,012 | A | 12/1983 | Stephenson et al. |
| 4,422,041 | A | 12/1983 | Lienau |
| 4,431,005 | A | 2/1984 | McCormick |
| 4,485,815 | A | 12/1984 | Amplatz |
| 4,506,676 | A | 3/1985 | Duska |
| 4,543,959 | A | 10/1985 | Sepponen |
| 4,548,208 | A | 10/1985 | Niemi |
| 4,571,834 | A | 2/1986 | Fraser et al. |
| 4,572,198 | A | 2/1986 | Codrington |
| 4,583,538 | A | 4/1986 | Onik et al. |
| 4,584,577 | A | 4/1986 | Temple |
| 4,584,994 | A | 4/1986 | Bamberger et al. |
| 4,608,977 | A | 9/1986 | Brown |
| 4,613,866 | A | 9/1986 | Blood |
| 4,617,925 | A | 10/1986 | Laitinen |
| 4,618,978 | A | 10/1986 | Cosman |
| 4,621,628 | A | 11/1986 | Bludermann |
| 4,625,718 | A | 12/1986 | Olerud et al. |
| 4,638,798 | A | 1/1987 | Shelden et al. |
| 4,642,786 | A | 2/1987 | Hansen |
| 4,645,343 | A | 2/1987 | Stockdale et al. |
| 4,649,504 | A | 3/1987 | Krouglicof et al. |
| 4,651,732 | A | 3/1987 | Frederick |
| 4,653,509 | A | 3/1987 | Oloff et al. |
| 4,659,971 | A | 4/1987 | Suzuki et al. |
| 4,660,970 | A | 4/1987 | Ferrano |
| 4,673,352 | A | 6/1987 | Hansen |
| 4,688,037 | A | 8/1987 | Krieg |
| 4,701,049 | A | 10/1987 | Beckman et al. |
| 4,705,395 | A | 11/1987 | Hageniers |
| 4,705,401 | A | 11/1987 | Addleman et al. |
| 4,706,665 | A | 11/1987 | Gouda |
| 4,709,156 | A | 11/1987 | Murphy et al. |
| 4,710,708 | A | 12/1987 | Rorden et al. |
| 4,719,419 | A | 1/1988 | Dawley |
| 4,722,056 | A | 1/1988 | Roberts et al. |
| 4,722,336 | A | 2/1988 | Kim et al. |
| 4,723,544 | A | 2/1988 | Moore et al. |
| 4,727,565 | A | 2/1988 | Ericson |
| RE32,619 | E | 3/1988 | Damadian |
| 4,733,969 | A | 3/1988 | Case et al. |
| 4,737,032 | A | 4/1988 | Addleman et al. |
| 4,737,794 | A | 4/1988 | Jones |
| 4,737,921 | A | 4/1988 | Goldwasser et al. |
| 4,742,356 | A | 5/1988 | Kuipers |
| 4,742,815 | A | 5/1988 | Ninan et al. |
| 4,743,770 | A | 5/1988 | Lee |
| 4,743,771 | A | 5/1988 | Sacks et al. |
| 4,745,290 | A | 5/1988 | Frankel et al. |
| 4,750,487 | A | 6/1988 | Zanetti |
| 4,753,528 | A | 6/1988 | Hines et al. |
| 4,761,072 | A | 8/1988 | Pryor |
| 4,764,016 | A | 8/1988 | Johansson |
| 4,771,787 | A | 9/1988 | Wurster et al. |
| 4,779,212 | A | 10/1988 | Levy |
| 4,782,239 | A | 11/1988 | Hirose et al. |
| 4,788,481 | A | 11/1988 | Niwa |
| 4,791,934 | A | 12/1988 | Brunnett |
| 4,793,355 | A | 12/1988 | Crum et al. |
| 4,794,262 | A | 12/1988 | Sato et al. |
| 4,797,907 | A | 1/1989 | Anderton |
| 4,803,976 | A | 2/1989 | Frigg et al. |
| 4,804,261 | A | 2/1989 | Kirschen |
| 4,805,615 | A | 2/1989 | Carol |
| 4,809,694 | A | 3/1989 | Ferrara |
| 4,821,200 | A | 4/1989 | Öberg |
| 4,821,206 | A | 4/1989 | Arora |
| 4,821,731 | A | 4/1989 | Martinelli et al. |
| 4,822,163 | A | 4/1989 | Schmidt |
| 4,825,091 | A | 4/1989 | Breyer et al. |
| 4,829,373 | A | 5/1989 | Leberl et al. |
| 4,836,778 | A | 6/1989 | Baumrind et al. |
| 4,838,265 | A | 6/1989 | Cosman et al. |
| 4,841,967 | A | 6/1989 | Chang et al. |
| 4,845,771 | A | 7/1989 | Wislocki et al. |
| 4,849,692 | A | 7/1989 | Blood |
| 4,860,331 | A | 8/1989 | Williams et al. |
| 4,862,893 | A | 9/1989 | Martinelli |
| 4,869,247 | A | 9/1989 | Howard, III et al. |
| 4,875,165 | A | 10/1989 | Fencil et al. |
| 4,875,478 | A | 10/1989 | Chen |
| 4,884,566 | A | 12/1989 | Mountz et al. |
| 4,889,526 | A | 12/1989 | Rauscher et al. |
| 4,896,673 | A | 1/1990 | Rose et al. |
| 4,905,698 | A | 3/1990 | Strohl, Jr. et al. |
| 4,923,459 | A | 5/1990 | Nambu |
| 4,931,056 | A | 6/1990 | Ghajar et al. |
| 4,945,305 | A | 7/1990 | Blood |
| 4,945,914 | A | 8/1990 | Allen |
| 4,951,653 | A | 8/1990 | Fry et al. |
| 4,955,891 | A | 9/1990 | Carol |
| 4,961,422 | A | 10/1990 | Marchosky et al. |
| 4,977,655 | A | 12/1990 | Martinelli |
| 4,989,608 | A | 2/1991 | Ratner |
| 4,991,579 | A | 2/1991 | Allen |
| 5,002,058 | A | 3/1991 | Martinelli |
| 5,005,592 | A | 4/1991 | Cartmell |
| 5,013,317 | A | 5/1991 | Cole et al. |
| 5,016,639 | A | 5/1991 | Allen |
| 5,017,139 | A | 5/1991 | Mushabac |
| 5,027,818 | A | 7/1991 | Bova et al. |
| 5,030,196 | A | 7/1991 | Inoue |
| 5,030,222 | A | 7/1991 | Calandruccio et al. |
| 5,031,203 | A | 7/1991 | Trecha |
| 5,042,486 | A | 8/1991 | Pfeiler et al. |
| 5,047,036 | A | 9/1991 | Koutrouvelis |
| 5,050,608 | A | 9/1991 | Watanabe et al. |
| 5,054,492 | A | 10/1991 | Scribner et al. |
| 5,057,095 | A | 10/1991 | Fabian |
| 5,059,789 | A | 10/1991 | Salcudean |
| 5,078,140 | A | 1/1992 | Kwoh |
| 5,079,699 | A | 1/1992 | Tuy et al. |

| Patent No. | Date | Inventor |
|---|---|---|
| 5,086,401 A | 2/1992 | Glassman et al. |
| 5,094,241 A | 3/1992 | Allen |
| 5,097,839 A | 3/1992 | Allen |
| 5,098,426 A | 3/1992 | Sklar et al. |
| 5,099,845 A | 3/1992 | Besz et al. |
| 5,099,846 A | 3/1992 | Hardy |
| 5,105,829 A | 4/1992 | Fabian et al. |
| 5,107,839 A | 4/1992 | Houdek et al. |
| 5,107,843 A | 4/1992 | Aarnio et al. |
| 5,107,862 A | 4/1992 | Fabian et al. |
| 5,109,194 A | 4/1992 | Cantaloube |
| 5,119,817 A | 6/1992 | Allen |
| 5,142,930 A | 9/1992 | Allen et al. |
| 5,143,076 A | 9/1992 | Hardy et al. |
| 5,152,288 A | 10/1992 | Hoenig et al. |
| 5,160,337 A | 11/1992 | Cosman |
| 5,161,536 A | 11/1992 | Vikomerson et al. |
| 5,178,164 A | 1/1993 | Allen |
| 5,178,621 A | 1/1993 | Cook et al. |
| 5,186,174 A | 2/1993 | Schlondorff et al. |
| 5,187,475 A | 2/1993 | Wagener et al. |
| 5,188,126 A | 2/1993 | Fabian et al. |
| 5,190,059 A | 3/1993 | Fabian et al. |
| 5,193,106 A | 3/1993 | DeSena |
| 5,197,476 A | 3/1993 | Nowacki et al. |
| 5,197,965 A | 3/1993 | Cherry et al. |
| 5,198,768 A | 3/1993 | Keren |
| 5,198,877 A | 3/1993 | Schulz |
| 5,207,688 A | 5/1993 | Carol |
| 5,211,164 A | 5/1993 | Allen |
| 5,211,165 A | 5/1993 | Dumoulin et al. |
| 5,211,176 A | 5/1993 | Ishiguro et al. |
| 5,212,720 A | 5/1993 | Landi et al. |
| 5,214,615 A | 5/1993 | Bauer |
| 5,219,351 A | 6/1993 | Teubner et al. |
| 5,222,499 A | 6/1993 | Allen et al. |
| 5,224,049 A | 6/1993 | Mushabac |
| 5,228,442 A | 7/1993 | Imran |
| 5,230,338 A | 7/1993 | Allen et al. |
| 5,230,623 A | 7/1993 | Guthrie et al. |
| 5,233,990 A | 8/1993 | Barnea |
| 5,237,996 A | 8/1993 | Waldman et al. |
| 5,249,581 A | 10/1993 | Horbal et al. |
| 5,251,127 A | 10/1993 | Raab |
| 5,251,635 A | 10/1993 | Dumoulin et al. |
| 5,253,647 A | 10/1993 | Takahashi et al. |
| 5,255,680 A | 10/1993 | Darrow et al. |
| 5,257,636 A | 11/1993 | White |
| 5,257,998 A | 11/1993 | Ota et al. |
| 5,261,404 A | 11/1993 | Mick et al. |
| 5,265,610 A | 11/1993 | Darrow et al. |
| 5,265,611 A | 11/1993 | Hoenig et al. |
| 5,269,759 A | 12/1993 | Hernandez et al. |
| 5,271,400 A | 12/1993 | Dumoulin et al. |
| 5,273,025 A | 12/1993 | Sakiyama et al. |
| 5,274,551 A | 12/1993 | Corby, Jr. |
| 5,279,309 A | 1/1994 | Taylor et al. |
| 5,285,787 A | 2/1994 | Machida |
| 5,291,199 A | 3/1994 | Overman et al. |
| 5,291,889 A | 3/1994 | Kenet et al. |
| 5,295,483 A | 3/1994 | Nowacki et al. |
| 5,297,549 A | 3/1994 | Beatty et al. |
| 5,299,253 A | 3/1994 | Wessels |
| 5,299,254 A | 3/1994 | Dancer et al. |
| 5,299,288 A | 3/1994 | Glassman et al. |
| 5,300,080 A | 4/1994 | Clayman et al. |
| 5,305,091 A | 4/1994 | Gelbart et al. |
| 5,305,203 A | 4/1994 | Raab |
| 5,306,271 A | 4/1994 | Zinreich et al. |
| 5,307,072 A | 4/1994 | Jones, Jr. |
| 5,309,913 A | 5/1994 | Kormos et al. |
| 5,315,630 A | 5/1994 | Sturm et al. |
| 5,316,024 A | 5/1994 | Hirschi et al. |
| 5,318,025 A | 6/1994 | Dumoulin et al. |
| 5,320,111 A | 6/1994 | Livingston |
| 5,325,728 A | 7/1994 | Zimmerman et al. |
| 5,325,873 A | 7/1994 | Hirschi et al. |
| 5,329,944 A | 7/1994 | Fabian et al. |
| 5,330,485 A | 7/1994 | Clayman et al. |
| 5,333,168 A | 7/1994 | Fernandes et al. |
| 5,353,795 A | 10/1994 | Souza et al. |
| 5,353,800 A | 10/1994 | Pohndorf et al. |
| 5,353,807 A | 10/1994 | DeMarco |
| 5,359,417 A | 10/1994 | Müller et al. |
| 5,368,030 A | 11/1994 | Zinreich et al. |
| 5,371,778 A | 12/1994 | Yanof et al. |
| 5,375,596 A | 12/1994 | Twiss et al. |
| 5,377,678 A | 1/1995 | Dumoulin et al. |
| 5,383,454 A | 1/1995 | Bucholz |
| 5,385,146 A | 1/1995 | Goldreyer |
| 5,385,148 A | 1/1995 | Lesh et al. |
| 5,386,828 A | 2/1995 | Owens et al. |
| 5,389,101 A | 2/1995 | Heilbrun et al. |
| 5,391,199 A | 2/1995 | Ben-Haim |
| 5,394,457 A | 2/1995 | Leibinger et al. |
| 5,394,875 A | 3/1995 | Lewis et al. |
| 5,397,329 A | 3/1995 | Allen |
| 5,398,684 A | 3/1995 | Hardy |
| 5,399,146 A | 3/1995 | Nowacki et al. |
| 5,400,384 A | 3/1995 | Fernandes et al. |
| 5,402,801 A | 4/1995 | Taylor |
| 5,408,409 A | 4/1995 | Glassman et al. |
| 5,413,573 A | 5/1995 | Koivukangas |
| 5,415,660 A | 5/1995 | Bechtold et al. |
| 5,417,210 A | 5/1995 | Funda et al. |
| 5,419,325 A | 5/1995 | Dumoulin et al. |
| 5,423,334 A | 6/1995 | Jordan |
| 5,425,367 A | 6/1995 | Shapiro et al. |
| 5,425,382 A | 6/1995 | Golden et al. |
| 5,426,683 A | 6/1995 | O—Farrell, Jr. et al. |
| 5,426,687 A | 6/1995 | Goodall et al. |
| 5,427,097 A | 6/1995 | Depp |
| 5,429,132 A | 7/1995 | Guy et al. |
| 5,433,198 A | 7/1995 | Desai |
| RE35,025 E | 8/1995 | Anderton |
| 5,437,277 A | 8/1995 | Dumoulin et al. |
| 5,443,066 A | 8/1995 | Dumoulin et al. |
| 5,443,489 A | 8/1995 | Ben-Haim |
| 5,444,756 A | 8/1995 | Pai et al. |
| 5,445,144 A | 8/1995 | Wodicka et al. |
| 5,445,150 A | 8/1995 | Dumoulin et al. |
| 5,445,166 A | 8/1995 | Taylor |
| 5,446,548 A | 8/1995 | Gerig et al. |
| 5,447,154 A | 9/1995 | Cinquin et al. |
| 5,448,610 A | 9/1995 | Yamamoto et al. |
| 5,453,686 A | 9/1995 | Anderson |
| 5,456,718 A | 10/1995 | Szymaitis |
| 5,457,641 A | 10/1995 | Zimmer et al. |
| 5,458,718 A | 10/1995 | Venkitachalam |
| 5,464,446 A | 11/1995 | Dreessen et al. |
| 5,466,261 A | 11/1995 | Richelsoph |
| 5,469,847 A | 11/1995 | Zinreich et al. |
| 5,478,341 A | 12/1995 | Cook et al. |
| 5,478,343 A | 12/1995 | Ritter |
| 5,480,422 A | 1/1996 | Ben-Haim |
| 5,480,439 A | 1/1996 | Bisek et al. |
| 5,483,961 A | 1/1996 | Kelly et al. |
| 5,485,849 A | 1/1996 | Panescu et al. |
| 5,487,391 A | 1/1996 | Panescu |
| 5,487,729 A | 1/1996 | Avellanet et al. |
| 5,487,757 A | 1/1996 | Truckai et al. |
| 5,490,196 A | 2/1996 | Rudich et al. |
| 5,494,034 A | 2/1996 | Schlondorff et al. |
| 5,503,416 A | 4/1996 | Aoki et al. |
| 5,513,637 A | 5/1996 | Twiss et al. |
| 5,514,146 A | 5/1996 | Lam et al. |

| | | | | | | |
|---|---|---|---|---|---|---|
| 5,515,160 A | | 5/1996 | Schulz et al. | 5,748,767 A | 5/1998 | Raab |
| 5,517,990 A | | 5/1996 | Kalfas et al. | 5,749,362 A | 5/1998 | Funda et al. |
| 5,531,227 A | | 7/1996 | Schneider | 5,749,835 A | 5/1998 | Glantz |
| 5,531,520 A | | 7/1996 | Grimson et al. | 5,752,513 A | 5/1998 | Acker et al. |
| 5,542,938 A | | 8/1996 | Avellanet et al. | 5,755,725 A | 5/1998 | Druais |
| 5,543,951 A | | 8/1996 | Moehrmann | RE35,816 E | 6/1998 | Schulz |
| 5,546,940 A | | 8/1996 | Panescu et al. | 5,758,667 A | 6/1998 | Slettenmark |
| 5,546,949 A | | 8/1996 | Frazin et al. | 5,762,064 A | 6/1998 | Polvani |
| 5,546,951 A | | 8/1996 | Ben-Haim | 5,767,669 A | 6/1998 | Hansen et al. |
| 5,551,429 A | | 9/1996 | Fitzpatrick et al. | 5,767,699 A | 6/1998 | Bosnyak et al. |
| 5,558,091 A | | 9/1996 | Acker et al. | 5,767,960 A | 6/1998 | Orman |
| 5,566,681 A | | 10/1996 | Manwaring et al. | 5,769,789 A | 6/1998 | Wang et al. |
| 5,568,384 A | | 10/1996 | Robb et al. | 5,769,843 A | 6/1998 | Abela et al. |
| 5,568,809 A | | 10/1996 | Ben-haim | 5,769,861 A | 6/1998 | Vilsmeier |
| 5,572,999 A | * | 11/1996 | Funda et al. ................ 600/118 | 5,772,594 A | 6/1998 | Barrick |
| 5,573,533 A | | 11/1996 | Strul | 5,775,322 A | 7/1998 | Silverstein et al. |
| 5,575,794 A | | 11/1996 | Walus et al. | 5,776,064 A | 7/1998 | Kalfas et al. |
| 5,575,798 A | | 11/1996 | Koutrouvelis | 5,782,765 A | 7/1998 | Jonkman |
| 5,583,909 A | | 12/1996 | Hanover | 5,787,886 A | 8/1998 | Kelly et al. |
| 5,588,430 A | | 12/1996 | Bova et al. | 5,792,055 A | 8/1998 | McKinnon |
| 5,590,215 A | | 12/1996 | Allen | 5,795,294 A | 8/1998 | Luber et al. |
| 5,592,939 A | | 1/1997 | Martinelli | 5,797,849 A | 8/1998 | Vesely et al. |
| 5,595,193 A | | 1/1997 | Walus et al. | 5,799,055 A | 8/1998 | Peshkin et al. |
| 5,596,228 A | | 1/1997 | Anderton et al. | 5,799,099 A | 8/1998 | Wang et al. |
| 5,600,330 A | | 2/1997 | Blood | 5,800,352 A | 9/1998 | Ferre et al. |
| 5,603,318 A | | 2/1997 | Heilbrun et al. | 5,800,535 A | 9/1998 | Howard, III |
| 5,611,025 A | | 3/1997 | Lorensen et al. | 5,802,719 A | 9/1998 | O'Farrell, Jr. et al. |
| 5,617,462 A | | 4/1997 | Spratt | 5,803,089 A | 9/1998 | Ferre et al. |
| 5,617,857 A | | 4/1997 | Chader et al. | 5,807,252 A | 9/1998 | Hassfeld et al. |
| 5,619,261 A | | 4/1997 | Anderton | 5,810,008 A | 9/1998 | Dekel et al. |
| 5,622,169 A | | 4/1997 | Golden et al. | 5,810,728 A | 9/1998 | Kuhn |
| 5,622,170 A | | 4/1997 | Schulz | 5,810,735 A | 9/1998 | Halperin et al. |
| 5,627,873 A | | 5/1997 | Hanover et al. | 5,820,553 A | 10/1998 | Hughes |
| 5,628,315 A | | 5/1997 | Vilsmeier et al. | 5,823,192 A | 10/1998 | Kalend et al. |
| 5,630,431 A | | 5/1997 | Taylor | 5,823,958 A | 10/1998 | Truppe |
| 5,636,644 A | | 6/1997 | Hart et al. | 5,824,085 A | 10/1998 | Sahay et al. |
| 5,638,819 A | * | 6/1997 | Manwaring et al. ......... 600/424 | 5,825,908 A | 10/1998 | Pieper et al. |
| 5,640,170 A | | 6/1997 | Anderson | 5,828,725 A | 10/1998 | Levinson |
| 5,642,395 A | | 6/1997 | Anderton et al. | 5,828,770 A | 10/1998 | Leis et al. |
| 5,643,268 A | | 7/1997 | Vilsmeier et al. | 5,829,444 A | 11/1998 | Ferre et al. |
| 5,645,065 A | | 7/1997 | Shapiro et al. | 5,830,222 A | * 11/1998 | Makower .................... 606/159 |
| 5,646,524 A | | 7/1997 | Gilboa | 5,831,260 A | 11/1998 | Hansen |
| 5,647,361 A | | 7/1997 | Damadian | 5,833,608 A | 11/1998 | Acker |
| 5,662,111 A | | 9/1997 | Cosman | 5,834,759 A | 11/1998 | Glossop |
| 5,664,001 A | | 9/1997 | Tachibana et al. | 5,836,954 A | 11/1998 | Heilbrun et al. |
| 5,674,296 A | | 10/1997 | Bryan et al. | 5,840,024 A | 11/1998 | Taniguchi et al. |
| 5,676,673 A | | 10/1997 | Ferre et al. | 5,840,025 A | 11/1998 | Ben-Haim |
| 5,681,260 A | | 10/1997 | Ueda et al. | 5,843,076 A | 12/1998 | Webster, Jr. et al. |
| 5,682,886 A | | 11/1997 | Delp et al. | 5,848,967 A | 12/1998 | Cosman |
| 5,682,890 A | | 11/1997 | Kormos et al. | 5,851,183 A | 12/1998 | Bucholz |
| 5,690,108 A | | 11/1997 | Chakeres | 5,865,846 A | 2/1999 | Bryan et al. |
| 5,694,945 A | | 12/1997 | Ben-Haim | 5,868,674 A | 2/1999 | Glowinski et al. |
| 5,695,500 A | | 12/1997 | Taylor et al. | 5,868,675 A | 2/1999 | Henrion et al. |
| 5,695,501 A | | 12/1997 | Carol et al. | 5,871,445 A | 2/1999 | Bucholz |
| 5,697,377 A | | 12/1997 | Wittkampf | 5,871,455 A | 2/1999 | Ueno |
| 5,702,406 A | | 12/1997 | Vilsmeier et al. | 5,871,487 A | 2/1999 | Warner et al. |
| 5,711,299 A | | 1/1998 | Manwaring et al. | 5,873,822 A | 2/1999 | Ferre et al. |
| 5,713,946 A | | 2/1998 | Ben-Haim | 5,882,304 A | 3/1999 | Ehnholm et al. |
| 5,715,822 A | | 2/1998 | Watkins et al. | 5,884,410 A | 3/1999 | Prinz |
| 5,715,836 A | | 2/1998 | Kliegis et al. | 5,889,834 A | 3/1999 | Vilsmeier et al. |
| 5,718,241 A | | 2/1998 | Ben-Haim et al. | 5,891,034 A | 4/1999 | Bucholz |
| 5,727,552 A | | 3/1998 | Ryan | 5,891,157 A | 4/1999 | Day et al. |
| 5,727,553 A | | 3/1998 | Saad | 5,904,691 A | 5/1999 | Barnett et al. |
| 5,729,129 A | | 3/1998 | Acker | 5,907,395 A | 5/1999 | Schultz et al. |
| 5,730,129 A | | 3/1998 | Darrow et al. | 5,913,820 A | 6/1999 | Bladen et al. |
| 5,730,130 A | | 3/1998 | Fitzpatrick et al. | 5,920,395 A | 7/1999 | Schulz |
| 5,732,703 A | | 3/1998 | Kalfas et al. | 5,921,992 A | 7/1999 | Costales et al. |
| 5,735,278 A | | 4/1998 | Hoult et al. | 5,923,727 A | 7/1999 | Navab |
| 5,738,096 A | | 4/1998 | Ben-Haim | 5,928,248 A | 7/1999 | Acker |
| 5,740,802 A | | 4/1998 | Nafis et al. | 5,938,603 A | 8/1999 | Ponzi |
| 5,741,214 A | | 4/1998 | Ouchi et al. | 5,938,694 A | 8/1999 | Jaraczewski et al. |
| 5,742,394 A | | 4/1998 | Hansen | 5,947,980 A | 9/1999 | Jensen et al. |
| 5,744,953 A | | 4/1998 | Hansen | 5,947,981 A | 9/1999 | Cosman |

| | | | |
|---|---|---|---|
| 5,950,629 A | 9/1999 | Taylor et al. | |
| 5,951,475 A | 9/1999 | Gueziec et al. | |
| 5,951,571 A | 9/1999 | Audette | |
| 5,954,647 A | 9/1999 | Bova et al. | |
| 5,957,844 A | 9/1999 | Dekel et al. | |
| 5,961,553 A | 10/1999 | Coty et al. | |
| 5,964,796 A | 10/1999 | Imran | |
| 5,967,980 A | 10/1999 | Ferre et al. | |
| 5,967,982 A | 10/1999 | Barnett | |
| 5,968,047 A | 10/1999 | Reed | |
| 5,971,997 A | 10/1999 | Guthrie et al. | |
| 5,976,156 A | 11/1999 | Taylor et al. | |
| 5,980,535 A | 11/1999 | Barnett et al. | |
| 5,983,126 A | 11/1999 | Wittkampf | |
| 5,987,349 A | 11/1999 | Schulz | |
| 5,987,960 A | 11/1999 | Messner et al. | |
| 5,999,837 A | 12/1999 | Messner et al. | |
| 5,999,840 A | 12/1999 | Grimson et al. | |
| 6,001,130 A | 12/1999 | Bryan et al. | |
| 6,006,126 A | 12/1999 | Cosman | |
| 6,006,127 A | 12/1999 | Van Der Brug et al. | |
| 6,013,087 A | 1/2000 | Adams et al. | |
| 6,014,580 A | 1/2000 | Blume et al. | |
| 6,016,439 A | 1/2000 | Acker | |
| 6,019,725 A | 2/2000 | Vesely et al. | |
| 6,024,695 A | 2/2000 | Taylor et al. | |
| 6,050,724 A | 4/2000 | Schmitz et al. | |
| 6,059,718 A | 5/2000 | Taniguchi et al. | |
| 6,063,022 A | 5/2000 | Ben-Haim | |
| 6,071,288 A | 6/2000 | Carol et al. | |
| 6,073,043 A | 6/2000 | Schneider | |
| 6,076,008 A | 6/2000 | Bucholz | |
| 6,096,050 A | 8/2000 | Audette | |
| 6,104,944 A | 8/2000 | Martinelli | |
| 6,118,845 A | 9/2000 | Simon et al. | |
| 6,122,538 A | 9/2000 | Sliwa, Jr. et al. | |
| 6,122,541 A * | 9/2000 | Cosman et al. | 606/130 |
| 6,131,396 A | 10/2000 | Duerr et al. | |
| 6,139,183 A | 10/2000 | Graumann | |
| 6,147,480 A | 11/2000 | Osadchy et al. | |
| 6,149,592 A | 11/2000 | Yanof et al. | |
| 6,156,067 A | 12/2000 | Bryan et al. | |
| 6,161,032 A | 12/2000 | Acker | |
| 6,165,181 A | 12/2000 | Heilbrun et al. | |
| 6,167,296 A | 12/2000 | Shahidi | |
| 6,172,499 B1 | 1/2001 | Ashe | |
| 6,175,756 B1 | 1/2001 | Ferre et al. | |
| 6,178,345 B1 | 1/2001 | Vilsmeier et al. | |
| 6,190,414 B1 | 2/2001 | Young et al. | |
| 6,194,639 B1 | 2/2001 | Botella et al. | |
| 6,201,387 B1 | 3/2001 | Govari | |
| 6,203,497 B1 | 3/2001 | Dekel et al. | |
| 6,205,411 B1 | 3/2001 | DiGioia et al. | |
| 6,211,666 B1 | 4/2001 | Acker | |
| 6,223,067 B1 | 4/2001 | Vilsmeier | |
| 6,233,476 B1 | 5/2001 | Strommer et al. | |
| 6,245,109 B1 | 6/2001 | Mendes et al. | |
| 6,246,231 B1 | 6/2001 | Ashe | |
| 6,259,942 B1 | 7/2001 | Westermann et al. | |
| 6,273,896 B1 | 8/2001 | Franck et al. | |
| 6,285,902 B1 * | 9/2001 | Kienzle et al. | 600/427 |
| 6,298,262 B1 | 10/2001 | Franck et al. | |
| 6,314,310 B1 | 11/2001 | Ben-Haim et al. | |
| 6,332,089 B1 | 12/2001 | Acker et al. | |
| 6,332,887 B1 | 12/2001 | Knox | |
| 6,341,231 B1 | 1/2002 | Ferre et al. | |
| 6,348,058 B1 * | 2/2002 | Melkent et al. | 606/130 |
| 6,351,659 B1 | 2/2002 | Vilsmeier | |
| 6,375,682 B1 | 4/2002 | Fleischmann et al. | |
| 6,381,485 B1 | 4/2002 | Hunter et al. | |
| 6,424,856 B1 | 7/2002 | Vilsmeier et al. | |
| 6,427,314 B1 | 8/2002 | Acker | |
| 6,428,547 B1 | 8/2002 | Vilsmeier et al. | |
| 6,434,415 B1 | 8/2002 | Foley et al. | |
| 6,437,567 B1 | 8/2002 | Schenck et al. | |
| 6,445,943 B1 | 9/2002 | Ferre et al. | |
| 6,466,261 B1 | 10/2002 | Nakamura et al. | |
| 6,470,207 B1 | 10/2002 | Simon et al. | |
| 6,474,341 B1 | 11/2002 | Hunter et al. | |
| 6,478,802 B2 | 11/2002 | Kienzle, III et al. | |
| 6,484,049 B1 | 11/2002 | Seeley et al. | |
| 6,490,475 B1 | 12/2002 | Seeley et al. | |
| 6,493,573 B1 | 12/2002 | Martinelli et al. | |
| 6,498,944 B1 | 12/2002 | Ben-Haim et al. | |
| 6,499,488 B1 | 12/2002 | Hunter et al. | |
| 6,516,046 B1 | 2/2003 | Fröhlich et al. | |
| 6,527,443 B1 | 3/2003 | Vilsmeier et al. | |
| 6,551,325 B2 | 4/2003 | Neubauer et al. | |
| 6,584,174 B2 | 6/2003 | Schubert et al. | |
| 6,609,022 B2 | 8/2003 | Vilsmeier et al. | |
| 6,611,700 B1 | 8/2003 | Vilsmeier et al. | |
| 6,640,128 B2 | 10/2003 | Vilsmeier et al. | |
| 6,694,162 B2 | 2/2004 | Hartlep | |
| 6,701,179 B1 | 3/2004 | Martinelli et al. | |
| 6,895,268 B1 * | 5/2005 | Rahn et al. | 600/429 |
| 6,947,786 B2 * | 9/2005 | Simon et al. | 600/427 |
| 2001/0007918 A1 | 7/2001 | Vilsmeier et al. | |
| 2002/0077540 A1 * | 6/2002 | Kienzle, III | 600/424 |
| 2002/0087163 A1 | 7/2002 | Dixon et al. | |
| 2002/0095081 A1 | 7/2002 | Vilsmeier | |
| 2003/0028196 A1 | 2/2003 | Bonutti | |
| 2003/0069591 A1 * | 4/2003 | Carson et al. | 606/130 |
| 2003/0120150 A1 | 6/2003 | Govari | |
| 2003/0194505 A1 | 10/2003 | Milbocker | |
| 2004/0024309 A1 | 2/2004 | Ferre et al. | |
| 2004/0097952 A1 * | 5/2004 | Sarin et al. | 606/102 |
| 2004/0236424 A1 | 11/2004 | Berez et al. | |
| 2004/0254584 A1 | 12/2004 | Sarin et al. | |
| 2005/0043621 A1 | 2/2005 | Perlin | |
| 2005/0254814 A1 | 11/2005 | Sakamoto | |

FOREIGN PATENT DOCUMENTS

| | | |
|---|---|---|
| DE | 3042343 A1 | 6/1982 |
| DE | 35 08730 | 3/1985 |
| DE | 37 17 871 | 5/1987 |
| DE | 38 38011 | 11/1988 |
| DE | 3831278 A1 | 3/1989 |
| DE | 42 13 426 | 4/1992 |
| DE | 42 25 112 | 7/1992 |
| DE | 4233978 C1 | 4/1994 |
| DE | 197 15 202 | 4/1997 |
| DE | 197 47 427 | 10/1997 |
| DE | 197 51 761 | 11/1997 |
| DE | 198 32 296 | 7/1998 |
| DE | 198 56 013 A | 6/2000 |
| DE | 100 13 519 A | 10/2001 |
| DE | 20111479 | 10/2001 |
| DE | 10085137 | 11/2002 |
| EP | 0 062 941 | 3/1982 |
| EP | 0 119 660 | 9/1984 |
| EP | 0 155 857 | 1/1985 |
| EP | 0 319 844 A1 | 1/1988 |
| EP | 0 326 768 | 12/1988 |
| EP | 0419729 A1 | 9/1989 |
| EP | 0350996 A1 | 1/1990 |
| EP | 0 651 968 A1 | 8/1990 |
| EP | 0 427 358 | 10/1990 |
| EP | 0 456 103 | 5/1991 |
| EP | 0 581 704 B1 | 7/1993 |
| EP | 0655138 B1 | 8/1993 |
| EP | 0894473 A2 | 1/1995 |
| EP | 0 820 731 A | 1/1998 |
| EP | 0 908 146 | 10/1998 |
| EP | 0 930 046 | 10/1998 |
| EP | 1 057 461 | 12/2000 |

| | | |
|---|---|---|
| EP | 1103229 | 5/2001 |
| EP | 1 188 421 A | 3/2002 |
| EP | 1 442 715 A | 8/2004 |
| FR | 2417970 | 2/1979 |
| FR | 2 618 211 | 7/1987 |
| GB | 1 243 353 A | 8/1971 |
| GB | 2 094 590 | 2/1982 |
| GB | 2 164 856 | 10/1984 |
| JP | 61-94639 | 10/1984 |
| JP | 62-327 | 6/1985 |
| JP | 63-240851 | 3/1987 |
| JP | 3-267054 | 3/1990 |
| JP | 2765738 | 4/1991 |
| WO | WO 88/09151 | 12/1988 |
| WO | WO 89/05123 | 6/1989 |
| WO | WO 90/05494 | 5/1990 |
| WO | WO 91/04711 | 4/1991 |
| WO | WO 9103982 | 4/1991 |
| WO | WO 91/07726 | 5/1991 |
| WO | WO 92/03090 | 3/1992 |
| WO | WO 92/06645 | 4/1992 |
| WO | WO 94/04938 | 3/1994 |
| WO | WO 94/23647 | 10/1994 |
| WO | WO 94/24933 | 11/1994 |
| WO | WO 95/07055 | 3/1995 |
| WO | WO 96/11624 | 4/1996 |
| WO | WO 96/32059 | 10/1996 |
| WO | WO 97/36192 | 10/1997 |
| WO | WO 97/49453 | 12/1997 |
| WO | WO 98/08554 | 3/1998 |
| WO | WO 98/38908 | 9/1998 |
| WO | WO 99/38449 | 1/1999 |
| WO | WO 99/15097 | 4/1999 |
| WO | WO 99/52094 | 4/1999 |
| WO | WO 99/21498 | 5/1999 |
| WO | WO 99/23956 | 5/1999 |
| WO | WO 99/26549 | 6/1999 |
| WO | WO 99/27839 | 6/1999 |
| WO | WO 99/29253 | 6/1999 |
| WO | WO 99/33406 | 7/1999 |
| WO | WO 99/37208 | 7/1999 |
| WO | WO 99/60939 | 12/1999 |
| WO | WO 00/23015 | 4/2000 |
| WO | WO 01/30437 A1 | 5/2001 |
| WO | WO-0176497 | 10/2001 |
| WO | WO02/37935 | 5/2002 |
| WO | WO-02067783 | 9/2002 |
| WO | WO03/039377 | 5/2003 |
| WO | WO 03/079940 | 10/2003 |

OTHER PUBLICATIONS

Bergstrom et al. Stereotaxic Computed Tomography, Am. J. Roentgenol, vol. 127 pp. 167-170 (1976).
Brown, R., M.D., A Stereotactic Head Frame for Use with CT Body Scanners, Investigative Radiology © J.B. Lippincott Company, pp. 300-304 (Jul.-Aug. 1979).
Bucholz, R.D., et al. Image-guided surgical techniques for infections and trauma of the central nervous system, Neurosurg. Clinics of N. A., vol. 7, No. 2, pp. 187-200 (1996).
Bucholz, R.D., et al., A Comparison of Sonic Digitizers Versus Light Emitting Diode-Based Localization, Interactive Image-Guided Neurosurgery, Chapter 16, pp. 179-200 (1993).
Bucholz, R.D., et al., Intraoperative localization using a three dimensional optical digitizer, SPIE—The Intl. Soc. for Opt. Eng., vol. 1894, pp. 312-322 (Jan. 17-19, 1993).
Bucholz, R.D., et al., Intraoperative Ultrasonic Brain Shift Monitor and Analysis, Stealth Station Marketing Brochure (2 pages) (undated).
Bucholz, R.D., et al., The Correction of Stereotactic Inaccuracy Caused by Brain Shift Using an Intraoperative Ultrasound Device, First Joint Conference, Computer Vision, Virtual Reality and Robot-ics in Medicine and Medical Robotics and Computer-Assisted Surgery, Grenoble, France, pp. 459-466 (Mar. 19-22, 1997).
Cutting M.D. et al., Optical Tracking of Bone Fragments During Craniofacial Surgery, Second Annual International Symposium on Medical Robotics and Computer Assisted Surgery, pp. 221-225, (Nov. 1995).
Friets, E.M., et al. A Frameless Stereotaxic Operating Microscope for Neurosurgery, IEEE Trans. on Biomed. Eng., vol. 36, No. 6, pp. 608-617 (Jul. 1989).
Gallen, C.C., et al., Intracranial Neurosurgery Guided by Functional Imaging, Surg. Neurol., vol. 42, pp. 523-530 (1994).
Galloway, R.L., Jr. et al, Optical localization for interactive, image-guided neurosurgery, SPIE, vol. 2164, pp. 137-145 (undated.
Galloway, R.L., et al., Interactive Image-Guided Neurosurgery, IEEE Trans. on Biomed. Eng., vol. 89, No. 12, pp. 1226-1231 (1992).
Gomez, C.R., et al., Transcranial Doppler Ultrasound Following Closed Head Injury: Vasospasm or Vasoparalysis?, Surg. Neurol., vol. 35, pp. 30-35 (1991).
Grimson, W.E.L., An Automatic Registration Method for Frameless Stereotaxy, Image Guided Surgery, and enhanced Reality Visualization, IEEE, pp. 430-436 (1994).
Grimson, W.E.L., et al., Virtual-reality technology is giving surgeons the equivalent of x-ray vision helping them to remove tumors more effectively, to minimize surgical wounds and to avoid damaging critical tissues, Sci. Amer., vol. 280, No. 6, pp. 62-69 (Jun. 1999).
Guthrie, B.L., Graphic-Interactive Cranial Surgery: The Operating Arm System, Handbook of Stereotaxy Using the CRW Apparatus, Chapter 13, pp. 193-211 (undated.
Hardy, T., M.D., et al., CASS: A Program for Computer Assisted Stereotaxic Surgery, The Fifth Annual Symposium on Comptuer Applications in Medical Care, Proceedings, Nov. 1-4, 1981, IEEE, pp. 1116-1126, (1981).
Heilbrun, M.D., Progressive Technology Applications, Neurosurgery for the Third Millenium, Chapter 15, J. Whitaker & Sons, Ltd., Amer. Assoc. of Neurol. Surgeons, pp. 191-198 (1992).
Heilbrun, M.P., Computed Tomography—Guided Stereotactic Systems, Clinical Neurosurgery, Chapter 31, pp. 564-581 (1983).
Heilbrun, M.P., et al., Stereotactic Localization and Guidance Using a Machine Vision Technique, Sterotact & Funct. Neurosurg., Proceed. of the Mtg. of the Amer. Soc. for Sterot. and Funct. Neurosurg. (Pittsburgh, PA) vol. 58, pp. 94-98 (1992).
Kall, B., The Impact of Computer and lmgaging Technology on Stereotactic Surgery, Proceedings of the Meeting of the American Society for Stereotactic and Functional Neurosurgery, pp. 10-22 (1987).
Kato, A., et al., A frameless, armless navigational system for computer-assisted neurosurgery, J. Neurosurg., vol. 74, pp. 845-849 (May 1991).
Kelly, P.J., Computer Assisted Stereotactic Biopsy and Volumetric Resection of Pediatric Brain Tumors, Brain Tumors in Children, Neurologic Clinics, vol. 9, No. 2, pp. 317-336 (May 1991).
Kelly, P.J., et al., Results of Computed Tomography-based Computer-assisted Stereotactic Resection of Metastatic Intracranial Tumors, Neurosurgery, vol. 22, No. 1, Part 1, 1988, pp. 7-17 (Jan. 1988).
Kelly, P.J., Computer-Directed Stereotactic Resection of Brain Tumors, Neurologica Operative Atlas, vol. 1, No. 4, pp. 299-313 (1991).
Kelly, P.J., Stereotactic Imaging, Surgical Planning and Computer-Assisted Resection of Intracranial Lesions: Methods and Results, Advances and Technical Standards in Neurosurgery, vol. 17, pp. 78-118, (1990).
Kim, W.S. et al., A Helmet Mounted Display for Telerobotics, IEEE, pp. 543-547 (1988).
Klimek, L., et al., Long-Term Experience with Different Types of Localization Systems in Skull-Base Surgery, Ear, Nose & Throat Surgery, Chapter 51, pp. 635-638 (undated).
Kosugi, Y., et al., An Articulated Neurosurgical Navigation System Using MRI and CT Images, IEEE Trans. on Biomed, Eng. vol. 35, No. 2, pp. 147-152 (Feb. 1988).

Krybus, W., et al., Navigation Support for Surgery by Means of Optical Position Detection, Computer Assisted Radiology Proceed. of the Intl. Symp. CAR '91 Computed Assisted Radiology, pp. 362-366 (Jul. 3-6, 1991).

Kwoh, Y.S., Ph.D., et al., A New Computerized Tomographic-Aided Robotic Stereotaxis System, Robotics Age, vol. 7, No. 6, pp. 17-22 (Jun. 1985).

Lavallee, S., et al., Computer Assisted Knee Anterior Cruciate Ligament Reconstruction First Clinical Tests, Proceedings of the First International Symposium on Medical Robotics and Computer Assisted Surgery, pp. 11-16 (Sep. 1994).

Lavallee, S., et al., Computer Assisted Medical Interventions, NATO ASI Series, vol. F 60, 3d Imaging in Medic., pp. 301-312 (1990).

Leavitt, D.D., et al., Dynamic Field Shaping to Optimize Stereotactic Radiosurgery, I.J. Rad. Onc. Biol. Physc., vol. 21, pp. 1247-1255 (1991).

Maurer, Jr., et al., Registration of Head CT Images to Physical Space Using a Weighted Combination of Points and Surfaces, IEEE Trans. on Med. Imaging, vol. 17, No. 5, pp. 753-761 (Oct. 1998).

McGirr, S., M.D., et al., Stereotactic Resection of Juvenile Pilocytic Astrocytomas of the Thalamus and Basal Ganglia, Neurosurgery, vol. 20, No. 3, pp. 447-452, (1987).

Ng, W.S. et al., Robotic Surgery—A First-Hand Experience in Transurethral Resection of the Prostate Surgery, IEEE Eng. in Med. and Biology, pp. 120-125 (Mar. 1993).

Penn, R.D., et al., Stereotactic Surgery with Image Processing of Computerized Tomographic Scans, Neurosurgery, vol. 3, No. 2, pp. 157-163 (Sep.-Oct. 1978).

Pixsys, 3-D Digitizing Accessories, by Pixsys (marketing brochure)(undated) (2 pages).

Reinhardt, H., et al., A Computer-Assisted Device for Intraoperative CT-Correlated Localization of Brain Tumors, pp. 51-58 (1988).

Reinhardt, H.F. et al., Sonic Stereometry in Microsurgical Procedures for Deep-Seated Brain Tumors and Vascular Malformations, Neurosurgery, vol. 32, No. 1, pp. 51-57 (Jan. 1993).

Reinhardt, H.F., et al., Mikrochirugische Entfernung tiefliegender Gefäβmirβbildungen mit Hilfe der Sonar-Stereometrie (Microsurgical Removal of Deep-Seated Vascular Malformations Using Sonar Stereometry). Ultraschall in Med. 12, pp. 80-83 (1991).

Reinhardt, Hans. F., Neuronavigation: A Ten-Year Review, Neurosurgery, pp. 329-341 (undated).

Simon, D.A., Accuracy Validation in Image-Guided Orthopaedic Surgery, Second Annual Intl. Symp. on Med. Rob. an Comp-Assisted surgery, MRCAS '95, pp. 185-192 (undated).

Smith, K.R., et al. Multimodality Image Analysis and Display Methods for Improved Tumor Localization in Stereotactic Neurosurgery, Annul Intl. Conf. of the IEEE Eng. in Med. and Biol. Soc., vol. 13, No. 1, p. 210 (1991).

Tan, K., Ph.D., et al., A frameless stereotactic approach to neurosurgical planning based on retrospective patient-image registration, J Neurosurgy, vol. 79, pp. 296-303 (Aug. 1993).

Thompson, et al., A System for Anatomical and Functional Mapping of the Human Thalamus, Computers and Biomedical Research, vol. 10, pp. 9-24 (1977).

Trobraugh, J.W., et al., Frameless Stereotactic Ultrasonography: Method and Applications, Computerized Medical Imaging and Graphics, vol. 18, No. 4, pp. 235-246 (1994).

Von Hanwhr et al., Foreword, Computerized Medical Imaging and Graphics, vol. 18, No. 4, pp. 225-228, (Jul.-Aug. 1994).

Wang, M.Y., et al., An Automatic Technique for Finding and Localizing Externally Attached Markers in CT and MR Volume Images of the Head, IEEE Trans. on Biomed. Eng., vol. 43, No. 6, pp. 627-637 (Jun. 1996).

Watanabe, E., M.D., et al., Open Surgery Assisted by the Neuronavigator, a Stereotactic, Articulated, Sensitive Arm, Neurosurgery, vol. 28, No. 6, pp. 792-800 (1991).

Partial European Search Report for Application No. EP 04 00 1428.

Benzel et al., "Magnetic Source Imaging: a Review of the Magnes System of Biomagnetic Technologies Incorporated," Neurosurgery, vol. 33, No. 2 (Aug. 1993), pp. 252-259.

Bucholz et al., "Variables affecting the accuracy of stereotactic localizationusing computerized tomography," Journal of Neurosurgery, vol. 79, Nov. 1993, pp. 667-673.

Heilbrun et al., "Preliminary experience with Brown-Roberts-Wells (BRW) computerized tomography stereotaxic guidance system," Journal of Neurosurgery, vol. 59, Aug. 1983, pp. 217-222.

Horner et al., "A Comparison of CT-Stereotaxic Brain Biopsy Techniques," Investigative Radiology, Sep.-Oct. 1984, pp. 367-373.

Kelly et al., "Computer-assisted stereotaxic laser resection of intraaxial brain neoplasms," Journal of Neurosurgery, vol. 64, Mar. 1986, pp. 427-439.

Laitinen et al., "An Adapter for Computed Tomography-Guided, Stereotaxis," Surg. Neurol., 1985, pp. 559-566.

Laitinen, "Noninvasive multipurpose stereoadapter," Neurological Research, Jun. 1987, pp. 137-141.

Smith et al., "The Neurostationn™—A Highly Accurate, Minimally Invasive Solution to Frameless Stereotactic Neurosurgery," Computerized Medical Imaging and Graphics, vol. 18, Jul.-Aug. 1994, pp. 247-256.

The Laitinen Stereotactic System, E2-E6.

Germano, "Instrumentation, Technique and Technology", Neurosurgery, vol. 37, No. 2, Aug., 1995, pp. 348-350.

Merloz, et al., "Computer Assisted Spine Surgery", Clinical Assisted Spine Surgery, No. 337, pp. 86-96.

Hatch, et al., "Reference-Display System for the Integration of CT Scanning and the Operating Microscope", Proceedings of the Eleventh Annual Northeast Bioengineering Conference, Mar. 14-15, 1985, pp. 252-254.

Bryan, "Bryan Cervical Disc System Single Level Surgical Technique", Spinal Dynamics, 2002, pp. 1-33.

"Prestige Cervical Disc System Surgical Technique", 12 pgs.

Adams et al., "Orientation Aid for Head and Neck Surgeons," Innov. Tech. Biol. Med., vol. 13, No. 4, 1992, pp. 409-424.

Barrick et al., "Prophylactic Intramedullary Fixation of the Tibia for Stress Fracture in a Professional Athlete," Journal of Orthopaedic Trauma, vol. 6, No. 2, pp. 241-244 (1992).

Barrick et al., "Technical Difficulties with the Brooker-Wills Nail in Acute Fractures of the Femur," Journal of Orthopaedic Trauma, vol. 4, No. 2, pp. 144-150 (1990).

Barrick, "Distal Locking Screw Insertion Using a Cannulated Drill Bit: Technical Note," Journal of Orthopaedic Trauma, vol. 7, No. 3, 1993, pp. 248-251.

Batnitzky et al., "Three-Dimensinal Computer Reconstructions of Brain Lesions from Surface Contours Provided by Computed Tomography: A Prospectus," Neurosurgery, vol. 11, No. 1, Part 1, 1982, pp. 73-84.

Bouazza-Marouf et al.; "Robotic-Assisted Internal Fixation of Femoral Fractures", IMECHE., pp. 51-58 (1995).

Brack et al., "Accurate X-ray Based Navigation in Computer-Assisted Orthopedic Surgery," CAR '98, pp. 716-722.

Champleboux et al., "Accurate Calibration of Cameras and Range Imaging Sensors: the NPBS Method," IEEE International Conference on Robotics and Automation, Nice, France, May 1992.

Champleboux, "Utilisation de Fonctions Splines pour la Mise au Point D'un Capteur Tridimensionnel sans Contact," Quelques Applications Medicales, Jul. 1991.

Cinquin et al., "Computer Assisted Medical Interventions," IEEE Engineering in Medicine and Biology, May/Jun. 1995, pp. 254-263.

Cinquin et al., "Computer Assisted Medical Interventions," International Advanced Robotics Programme, Sep. 1989, pp. 63-65.

Clarysse et al., "A Computer-Assisted System for 3-D Frameless Localization in Stereotaxic MRI," IEEE Transactions on Medical Imaging, vol. 10, No. 4, Dec. 1991, pp. 523-529.

Feldmar et al., "3D-2D Projective Registration of Free-Form Curves and Surfaces," Rapport de recherche (Inria Sophia Antipolis), 1994, pp. 1-44.

Foley et al., "Fundamentals of Interactive Computer Graphics," The Systems Programming Series, Chapter 7, Jul. 1984, pp. 245-266.

Foley et al., "Image-guided Intraoperative Spinal Localization," Intraoperative Neuroprotection, Chapter 19, 1996, pp. 325-340.

Foley, "The SteathStation: Three-Dimensional Image-Interactive Guidance for the Spine Surgeon," Spinal Frontiers, Apr. 1996, pp. 7-9.

Gildenberg et al., "Calculation of Stereotactic Coordinates from the Computed Tomographic Scan," Neurosurgery, vol. 10, No. 5, May 1982, pp. 580-586.

Gonzalez, "Digital Image Fundamentals," Digital Image Processing, Second Edition, 1987, pp. 52-54.

Gottesfeld Brown et al., "Registration of Planar Film Radiographs with Computer Tomography," Proceedings of MMBIA, Jun. 1996, pp. 42-51.

Gueziec et al., "Registration of Computed Tomography Data to a Surgical Robot Using Fluoroscopy: A Feasibility Study," Computer Science/Mathematics, Sep. 27, 1996, 6 pages.

Hamadeh et al, "Kinematic Study of Lumbar Spine Using Functional Radiographies and 3D/2D Registration," TIMC UMR 5525—IMAG.

Hamadeh et al., "Automated 3-Dimensional Computed Tomographic and Fluorscopic Image Registration," Computer Aided Surgery (1998), 3:11-19.

Hamadeh et al., "Towards Automatic Registration Between CT and X-ray Images: Cooperation Between 3D/2D Registration and 2D Edge Detection," MRCAS '95, pp. 39-46.

Hatch, "Reference-Display System for the Integration of CT Scanning and the Operating Microscope," Thesis, Thayer School of Engineering, Oct. 1984, pp. 1-189.

Henderson et al., "An Accurate and Ergonomic Method of Registration for Image-guided Neurosurgery," Computerized Medical Imaging and Graphics, vol. 18, No. 4, Jul.-Aug. 1994, pp. 273-277.

Hoerenz, "The Operating Microscope I. Optical Principles, Illumination Systems, and Support Systems," Journal of Microsurgery, vol. 1, 1980, pp. 364-369.

Hofstetter et al., "Fluoroscopy Based Surgical Navigation—Concept and Clinical Applications," Computer Assisted Radiology and Surgery, 1997, pp. 956-960.

Hounsfield, "Computerized transverse axial scanning (tomography): Part 1. Description of system," British Journal of Radiology, vol. 46, No. 552, Dec. 1973, pp. 1016-1022.

Jacques et al., "A Computerized Microstereotactic Method to Approach, 3-Dimensionally Reconstruct, Remove and Adjuvantly Treat Small CNS Lesions," Applied Neurophysiology, vol. 43, 1980, pp. 176-182.

Jacques et al., "Computerized three-dimensional stereotaxic removal of small central nervous system lesions in patients," J. Neurosurg., vol. 53, Dec. 1980, pp. 816-820.

Joskowicz et al., "Computer-Aided Image-Guided Bone Fracture Surgery: Concept and Implementation," CAR '98, pp. 710-715.

Kelly et al., "Precision Resection of Intra-Axial CNS Lesions by CT-Based Stereotactic Craniotomy and Computer Monitored $CO_2$ Laser," Acta Neurochirurgica, vol. 68, 1983, pp. 1-9.

Lavallee et al, "Matching 3-D Smooth Surfaces with their 2-D Projections using 3-D Distance Maps," SPIE, vol. 1570, Geometric Methods in Computer Vision, 1991, pp. 322-336.

Lavallee et al., "Computer Assisted Driving of a Needle into the Brain," Proceedings of the International Symposium CAR '89, Computer Assisted Radiology, 1989, pp. 416-420.

Lavallee et al., "Computer Assisted Interventionist Imaging: The Instance of Stereotactic Brain Surgery," North-Holland MEDINFO 89, Part 1, 1989, pp. 613-617.

Lavallee et al., "Computer Assisted Spine Surgery: A Technique For Accurate Transpedicular Screw Fixation Using CT Data and a 3-0 Optical Localizer," TIMC, Faculte de Medecine de Grenoble.

Lavallee et al., "Image guided operating robot: a clinical application in stereotactic neurosurgery," Proceedings of the 1992 IEEE International Conference on Robotics and Automation, May 1992, pp. 618-624.

Lavallee et al., "Matching of Medical Images for Computed and Robot Assisted Surgery," IEEE EMBS, Orlando, 1991.

Lavallee, "A New System for Computer Assisted Neurosurgery," IEEE Engineering in Medicine & Biology Society 11th Annual International Conference, 1989, pp. 0926-0927.

Lavallee, "VI Adaption de la Methodologie a Quelques Applications Cliniques," Chapitre VI, pp. 133-148.

Leksell et al., "Stereotaxis and Tomography—A Technical Note," ACTA Neurochirurgica, vol. 52, 1980, pp. 1-7.

Lemieux et al., "A Patient-to-Computed-Tomography Image Registration Method Based on Digitally Reconstructed Radiographs," Med. Phys. 21(11), Nov. 1994, pp. 1749-1760.

Levin et al., "The Brain: Integrated Three-dimensional Display of MR and PET Images," Radiology, vol. 172, No. 3, Sep. 1989, pp. 783-789.

Mazier et al., "Computer-Assisted Interventionist Imaging: Application to the Vertebral Column Surgery," Annual International Conference of the IEEE Engineering in Medicine and Biology Society, vol. 12, No. 1, 1990, pp. 0430-0431.

Mazier et al., Chirurgie de la Colonne Vertebrale Assistee par Ordinateur: Appication au Vissage Pediculaire, Innov. Tech. Biol. Med., vol. 11, No. 5, 1990, pp. 559-566.

Pelizzari et al., "Accurate Three-Dimensional Registration of CT, PET, and/or MR Images of the Brain," Journal of Computer Assisted Tomography, Jan./Feb. 1989, pp. 20-26.

Pelizzari et al., "Interactive 3D Patient-Image Registration," Information Processing in Medical Imaging, 12th International Conference, IPMI '91, Jul. 7-12, 136-141 (A.C.F. Colchester et al. eds. 1991).

Pelizzari et al., No. 528—"Three Dimensional Correlation of PET, CT and MRI Images," The Journal of Nuclear Medicine, vol. 28, No. 4, Apr. 1987, p. 682.

Phillips et al., "Image Guided Orthopaedic Surgery Design and Analysis," Trans Inst. MC, vol. 17, No. 5, 1995, pp. 251-264.

Potamianos et al., "Intra-Operative Imaging Guidance for Keyhole Surgery Methodology and Calibration," First International Symposium on Medical Robotics and Computer Assisted Surgery, Sep. 22-24, 1994, pp. 98-104.

Reinhardt et al., "CT-Guided 'Real Time' Stereotaxy," ACTA Neurochirurgica, 1989.

Roberts et al., "A frameless stereotaxic integration of computerized tomographic imaging and the operating microscope," J. Neurosurg., vol. 65, Oct. 1986, pp. 545-549.

Rosenbaum et al., "Computerized Tomography Guided Stereotaxis: A New Approach," Applied Neurophysiology, vol. 43, No. 3-5, 1980, pp. 172-173.

Sautot, "Vissage Pediculaire Assiste Par Ordinateur," Sep. 20, 1994.

Schueler et al., "Correction of Image Intensifier Distortion for Three-Dimensional X-Ray Angiography," SPIE Medical Imaging 1995, vol. 2432, pp. 272-279.

Selvik et al., "A Roentgen Stereophotogrammetric System," Acta Radiologica Diagnosis, 1983, pp. 343-352.

Shelden et al., "Development of a computerized microsteroetaxic method for localization and removal of minute CNS lesions under direct 3-D vision," J. Neurosurg., vol. 52, 1980, pp. 21-27.

Smith et al., "Computer Methods for Improved Diagnostic Image Display Applied to Stereotactic Neurosurgey," Automedical, vol. 14, 1992, pp. 371-382.

Viant et al., "A Computer Assisted Orthopaedic System for Distal Locking of Intramedullary Nails," Proc. of MediMEC '95, Bristol, 1995, pp. 86-91.

Watanabe et al., "Three-Dimensional Digitizer (Neuronavigator): New Equipment for Computed Tomography-Guided Stereotaxic Surgery," Surgical Neurology, vol. 27, No. 6, Jun. 1987, pp. 543-547.

Watanabe, "Neuronavigator," Igaku-no-Ayumi, vol. 137, No. 6, May 10, 1986, pp. 1-4.

Weese et al., "An Approach to 2D/3D Registration of a Vertebra in 2D X-ray Fluoroscopies with 3D CT Images," pp. 119-128.

The Partial European Search Report mailed Apr. 23, 2008 for European Patent Application No. EP 07 11 1195 has been provided.

* cited by examiner

SIX DEGREE OF FREEDOM ALIGNMENT DISPLAY FOR MEDICAL PROCEDURES

FIELD OF THE INVENTION

The present invention generally relates to displays for use in medical procedures, and more specifically, to a six degree of freedom alignment display that includes indicia of the six degrees of freedom to assist in performing medical procedures.

BACKGROUND OF THE INVENTION

Image guided medical and surgical procedures utilize patient images obtained prior to or during a medical procedure to guide a physician performing the procedure. Recent advances in imaging technology, especially in imaging technologies that produce highly-detailed, computer-generated two-dimensional and three-dimensional images, such as computed tomography (CT), magnetic resonance imaging (MRI), isocentric C-arm fluoroscopic imaging or two and three-dimensional fluoroscopes or ultrasounds have increased the interest in image guided medical procedures.

During these image guided medical procedures, the area of interest of the patient that has been imaged is displayed on a two-dimensional display. Surgical instruments that are used during this medical procedure are tracked and superimposed onto this two-dimensional display to show the location of the surgical instrument relative to the area of interest in the body. However, these two-dimensional displays are not capable of providing either five or six degrees of freedom information of the instrument or other devices navigated in the body, which may be information in certain medical procedures.

Other types of navigation systems operate as an image-less system, where an image of the body is not captured by an imaging device prior to the medical procedure. With this type of procedure, the system may use a probe to contact certain landmarks in the body, such as landmarks on bone, where the system generates either a two-dimensional or three-dimensional model of the area of interest based upon these contacts. This way, when the surgical instrument or other object is tracked relative to this area, they can be superimposed on this model. Here again, however, the display that illustrates the tracked medical instrument in relation to this model is not capable of providing five or six degree of freedom information.

Moreover, in certain medical procedures providing either a five or six degree of freedom display, will greatly assist the surgeon in the medical procedure. For example, this type of information may be helpful with minimally invasive procedures where clearance and viewing of the area of interest may not be relatively available. Therefore, during these types of procedures, the surgeon may not clearly know where the tip or orientation of the instrument may be relative to the patient. With flexible instruments, such as catheters, it makes it even more difficult to estimate where the tip or orientation of the catheter may be during these types of procedures.

Still other procedures, such as orthopedic procedures, employ implants that include multiple components that articulate with one another. Placement of one component of the implant relative to another component of the implant is critical. If a display can provide both targeting and six degree of freedom information in relation to these mutually dependent components, these procedures may be improved. For example, each implant component may require a specific orientation relative to its corresponding implant component to provide for the proper placement and proper range of motion. With these types of procedures and implants, it is generally difficult to accurately locate the components in the five or six degrees of freedom position. Since the orientation and location of these individual components is dependent upon one another to be effective, these components must be properly positioned and aligned in order to improve the life of the implant, increase the range of motion and provide superior patient outcomes.

It is, therefore, desirable to provide a display, which can provide five or six degrees of freedom alignment information regarding tracked surgical instruments and implants, particularly implants or devices that have several components each having a specific orientation dependent upon one another. It is, therefore, an object of the present invention to provide such a display to assist in medical procedures.

SUMMARY OF THE INVENTION

In accordance with the teachings of the present invention, a six degree of freedom alignment display that includes indicia of at least five degree of freedom information to assist in performing a medical procedure is disclosed. The six degree of freedom display assists in various types of medical procedures, including orthopedic procedures, neurovascular, intravascular, spinal, cardiovascular procedures, soft tissue procedures, etc.

In an embodiment, a display for use in guiding a medical device to a target in a patient during a medical procedure includes indicia. This indicia includes first, second, third, fourth, and fifth indicia illustrated on the display that identifies first, second, third, fourth, and fifth degree of freedom information. These indicias are illustrated on the display to assist in guiding the medical device to the target.

In another embodiment, a navigation system for use in guiding a medical device to a target in a patient during a medical procedure includes a tracking sensor, a tracking device and a display. The tracking sensor is associated with the medical device and is operable to be used to track the medical device. The tracking device is operable to track the medical device with the tracking sensor. The display includes indicia illustrating at least five degree of freedom information and indicia of the medical device in relation to the at least five degree of freedom information.

In yet another embodiment, a method for navigation and displaying a medical device during a medical procedure is provided. This method includes selecting a target for navigating the medical device to, displaying the target in a coordinate system, tracking the medical device, and displaying the medical device in relation to the target with at least five degree of freedom information.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiment(s) is merely exemplary in nature and is in no way intended to limit the invention, its application, or uses. Moreover, while the invention is discussed in detail below in regard to an orthopedic surgical procedure, the display of the present invention may be used with any type of medical procedure, including orthopedic, cardiovascular, neurovascular, soft tissue procedures, or any other medical procedures.

Figure 1:
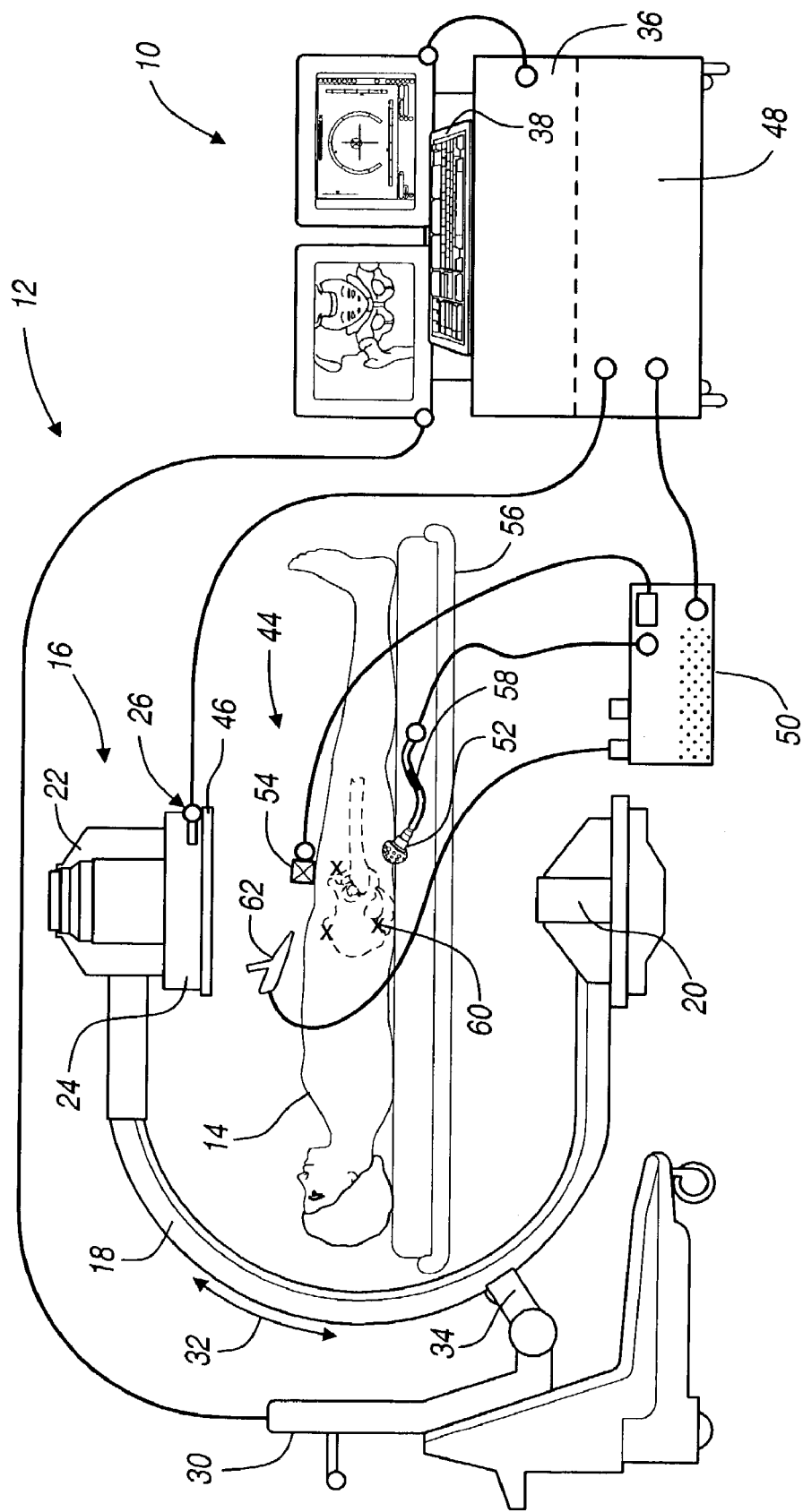
FIG. 1 is a diagram of a navigation system employing the display according to the teachings of the present invention.

FIG. 1 is a diagram illustrating the five or six degree of freedom (5 or 6 DOF) alignment display 10 employed with an image guided navigation system 12 for use in navigating a surgical instrument or implant during a medical procedure. It should also be noted that the display 10 of the present invention may be used or employed in an image-less based navigation system, further discussed herein. The navigation system 12 may be used to navigate any type of instrument or delivery system, such as a reamer, impactor, cutting block, saw blade, catheter, guide wires, needles, drug delivery systems, and cell delivery systems. The navigation system 12 may also be used to navigate any type of implant including orthopedic implants, spinal implants, cardiovascular implants, neurovascular implants, soft tissue implants, or any other devices implanted in a patient 14. The navigation system 12 may also be used to navigate implants or devices that are formed as an assembly or from multiple components where the location and orientation of each component is dependent upon one another to be effective in its use. For example, during a spinal procedure, the display may be used to track and align a spinal screw with a spinal rod to insure attachment of each device.

The navigation system 12 includes an imaging device 16 that is used to acquire pre-operative or real-time images of the patient 14. The imaging device 16 is a fluoroscopic C-arm x-ray imaging device that includes a C-arm 18, an x-ray source 20, an x-ray receiving section 22, an optional calibration and tracking target 24 and optional radiation sensors 26. The optional calibration and tracking target 24 includes calibration markers 28 (see FIGS. 2a-2b), further discussed herein. A C-arm controller 30 captures the x-ray images received at the receiving section 22 and stores the images for later use. The C-arm controller 30 may also control the rotation of the C-arm 18. For example, the C-arm 18 may move in the direction of arrow 32 or rotate about the long axis of the patient 14, allowing anterior or lateral views of the patient 14 to be imaged. Each of these movements involve rotation about a mechanical axis 34 of the C-arm 18. In this example, the long axis of the patient 14 is substantially in line with the mechanical axis 34 of the C-arm 18. This enables the C-arm 18 to be rotated relative to the patient 14, allowing images of the patient 14 to be taken from multiple directions or about multiple planes. An example of a fluoroscopic C-arm x-ray imaging device 16 is the "Series 9600 Mobile Digital Imaging System," from OEC Medical Systems, Inc., of Salt Lake City, Utah. Other exemplary fluoroscopes include bi-plane fluoroscopic systems, ceiling fluoroscopic systems, cath-lab fluoroscopic systems, fixed C-arm fluoroscopic systems, etc.

In operation, the imaging device 16 generates x-rays from the x-ray source 20 that propagate through the patient 14 and calibration and/or tracking target 24, into the x-ray receiving section 22. The receiving section 22 generates an image representing the intensities of the received x-rays. Typically, the receiving section 22 includes an image intensifier that first converts the x-rays to visible light and a charge coupled device (CCD) video camera that converts the visible light into digital images. Receiving section 22 may also be a digital device that converts x-rays directly to digital images, thus potentially avoiding distortion introduced by first converting to visible light. With this type of digital C-arm, which is generally a flat panel device, the calibration and/or tracking target 24 and the calibration process discussed below may be eliminated. Also, the calibration process may be eliminated for different types of medical procedures. Alternatively, the imaging device 16 may only take a single image with the calibration and tracking target 24 in place. Thereafter, the calibration and tracking target 24 may be removed from the line-of-sight of the imaging device 16.

Two dimensional fluoroscopic images taken by the imaging device 16 are captured and stored in the C-arm controller 30. These images are forwarded from the C-arm controller 30 to a controller or work station 36 having the display 10 that may either include a single display 10 or a dual display 10 and a user interface 38. The work station 36 provides facilities for displaying on the display 10, saving, digitally manipulating, or printing a hard copy of the received images, as well as the five or six degree of freedom display. The user interface 38, which may be a keyboard, joy stick, mouse, touch pen, touch screen or other suitable device allows a physician or user to provide inputs to control the imaging device 16, via the C-arm controller 30, or adjust the display settings, such as safe zones of the display 10, further discussed herein. The work station 36 may also direct the C-arm controller 30 to adjust the rotational axis 34 of the C-arm 18 to obtain various two-dimensional images along different planes in order to generate representative two-dimensional and three-dimensional images. When the x-ray source 20 generates the x-rays that propagate to the x-ray receiving section 22, the radiation sensors 26 sense the presence of radiation, which is forwarded to the C-arm controller 30, to identify whether or not the imaging device 16 is actively imaging. This information is also transmitted to a coil array controller 48, further discussed herein. Alternatively, a person or physician may manually indicate when the imaging device 16 is actively imaging or this function can be built into the x-ray source 20, x-ray receiving section 22, or the control computer 30.

Figure 2B:
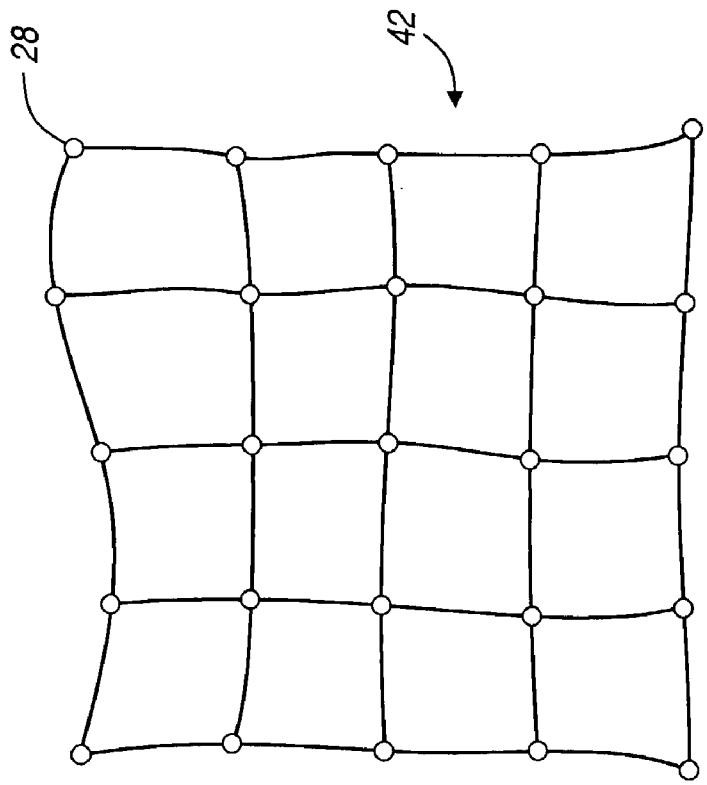
FIGS. 2a and 2b are diagrams representing undistorted and distorted views of a fluoroscopic C-arm imaging device.
Figure 2A:
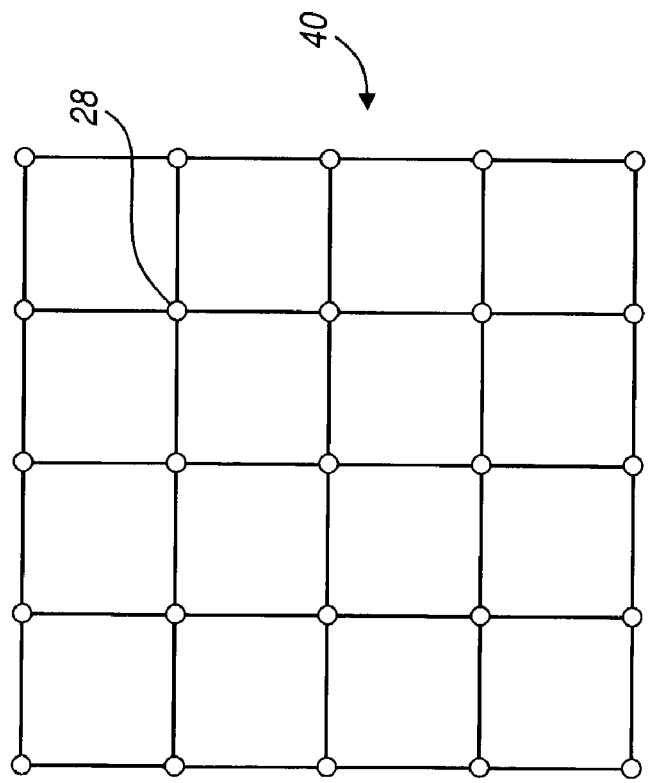

Fluoroscopic C-arm imaging devices 16 that do not include a digital receiving section 22 generally require the calibration and/or tracking target 24. This is because the raw images generated by the receiving section 22 tend to suffer from undesirable distortion caused by a number of factors, including inherent image distortion in the image intensifier and external electromagnetic fields. An empty undistorted or ideal image and an empty distorted image are shown in FIGS. 2a and 2b, respectively. The checkerboard shape, shown in FIG. 2a, represents the ideal image 40 of the checkerboard arranged calibration markers 28. The image taken by the receiving section 22, however, can suffer from distortion, as illustrated by the distorted calibration marker image 42, shown in FIG. 2b.

Intrinsic calibration, which is the process of correcting image distortion in a received image and establishing the projective transformation for that image, involves placing the calibration markers 28 in the path of the x-ray, where the calibration markers 28 are opaque or semi-opaque to the x-rays. The calibration markers 28 are rigidly arranged in pre-determined patterns in one or more planes in the path of the x-rays and are visible in the recorded images. Because the true relative position of the calibration markers 28 in the recorded images are known, the C-arm controller 30 or the work station or computer 36 is able to calculate an amount of distortion at each pixel in the image (where a pixel is a single point in the image). Accordingly, the computer or work station 36 can digitally compensate for the distortion in the image and generate a distortion-free or at least a distortion improved image 40 (see FIG. 2a). A more detailed explanation of exemplary methods for performing intrinsic calibration are described in the references: B. Schuele, et al., "Correction of Image Intensifier Distortion for Three-Dimensional Reconstruction," presented at SPIE Medical Imaging, San Diego, Calif. 1995; G. Champleboux, et al., "Accurate Calibration of Cameras and Range Imaging Sensors: the NPBS Method," Proceedings of the IEEE International Conference on Robotics and Automation, Nice, France, May, 1992; and U.S. Pat. No. 6,118,845, entitled "System And Methods For The Reduction And Elimination Of Image Artifacts In The Calibration Of X-Ray Imagers," issued Sep. 12, 2000, the contents of which are each hereby incorporated by reference.

While the fluoroscopic C-arm imaging device 16 is shown in FIG. 1, any other alternative imaging modality may also be used or an image-less based application may also be employed, as further discussed herein. For example, isocentric fluoroscopy, bi-plane fluoroscopy, ultrasound, computed tomography (CT), multi-slice computed tomography (MSCT), magnetic resonance imaging (MRI), high frequency ultrasound (HIFU), optical coherence tomography (OCT), intra-vascular ultrasound (IVUS), 2D, 3D or 4D ultrasound, or intraoperative CT or MRI may also be used to acquire pre-operative or real-time images or image data of the patient 14. Image datasets from hybrid modalities, such as positron emission tomography (PET) combined with CT, or single photon emission computer tomography (SPECT) combined with CT, could also provide functional image data superimposed onto anatomical data to be used to confidently reach target sights within the areas of interest. It should further be noted that the fluoroscopic C-arm imaging device 16, as shown in FIG. 1, provides a virtual bi-plane image using a single-head C-arm fluoroscope 16 by simply rotating the C-arm 18 about at least two planes, which could be orthogonal planes to generate two-dimensional images that can be converted to three-dimensional volumetric images that can be displayed on the six degree of freedom display 10.

The navigation system 12 further includes an electromagnetic navigation or tracking system 44 that includes a transmitter coil array 46, the coil array controller 48, a navigation probe interface 50, an instrument 52 having an electromagnetic tracker and a dynamic reference frame 54. It should further be noted that the entire tracking system 44 or parts of the tracking system 44 may be incorporated into the imaging device 16, including the work station 36 and radiation sensors 26. Incorporating the tracking system 44 will provide an integrated imaging and tracking system. Any combination of these components may also be incorporated into the imaging system 16, which again can include a fluoroscopic C-arm imaging device or any other appropriate imaging device. Obviously, if an image-less procedure is performed, the navigation and tracking system 44 will be a stand alone unit.

The transmitter coil array 46 is shown attached to the receiving section 22 of the C-arm 18. However, it should be noted that the transmitter coil array 46 may also be positioned at any other location as well, particularly if the imaging device 16 is not employed. For example, the transmitter coil array 46 may be positioned at the x-ray source 20, within the OR table 56 positioned below the patient 14, on siderails associated with the OR table 56, or positioned on the patient 14 in proximity to the region being navigated, such as by the patient's pelvic area. The transmitter coil array 46 includes a plurality of coils that are each operable to generate distinct electromagnetic fields into the navigation region of the patient 14, which is sometimes referred to as patient space. Representative electromagnetic systems are set forth in U.S. Pat. No. 5,913,820, entitled "Position Location System," issued Jun. 22, 1999 and U.S. Pat. No. 5,592,939, entitled "Method and System for Navigating a Catheter Probe," issued Jan. 14, 1997, each of which are hereby incorporated by reference.

The transmitter coil array 46 is controlled or driven by the coil array controller 48. The coil array controller 48 drives each coil in the transmitter coil array 46 in a time division multiplex or a frequency division multiplex manner. In this regard, each coil may be driven separately at a distinct time or all of the coils may be driven simultaneously with each being driven by a different frequency. Upon driving the coils in the transmitter coil array 46 with the coil array controller 48, electromagnetic fields are generated within the patient 14 in the area where the medical procedure is being performed, which is again sometimes referred to as patient space. The electromagnetic fields generated in the patient space induces currents in sensors 58 positioned in the instrument 52, further discussed herein. These induced signals from the instrument 52 are delivered to the navigation probe interface 50 and subsequently forwarded to the coil array controller 48. The navigation probe interface 50 provides all the necessary electrical isolation for the navigation system 12. The navigation probe interface 50 also includes amplifiers, filters and buffers required to directly interface with the sensors 58 in instrument 52. Alternatively, the instrument 52 may employ a wireless communications channel as opposed to being coupled directly to the navigation probe interface 50.

The instrument 52 is equipped with at least one, and may include multiple localization sensors 58. In this regard, the instrument 52 may include an orthogonal pair coil sensor 58 or a tri-axial coil sensor 58 or multiple single coil sensors 58 positioned about the instrument 52. Here again, the instrument 52 may be any type of medical instrument or implant. For example, the instrument may be a catheter that can be used to deploy a medical lead, be used for tissue ablation, or be used to deliver a pharmaceutical agent. The instrument 52 may also be an orthopedic instrument, used for an orthopedic procedure, such as reamers, impactors, cutting blocks, saw blades, drills, etc. The instrument 52 may also be any type of neurovascular instrument, cardiovascular instrument, soft tissue instrument, etc. Finally, the instrument 52 may be an implant that is tracked, as well as any other type of device positioned and located within the patient 14. These implants can include orthopedic implants, neurovascular implants, cardiovascular implants, soft tissue implants, or any other devices that are implanted into the patient 14. Particularly, implants that are formed from multiple components where the location and orientation of each component is dependent upon the location and orientation of the other component, such that each of these components can be tracked or navigated by the navigation and tracking system 44 to be displayed on the six degree of freedom display 10.

In an alternate embodiment, the electromagnetic sources or generators may be located within the instrument 52 and one or more receiver coils may be provided externally to the patient 14 forming a receiver coil array similar to the transmitter coil array 46. In this regard, the sensor coils 58 would generate electromagnetic fields, which would be received by the receiving coils in the receiving coil array similar to the transmitter coil array 46. Other types of localization or tracking may also be used with other types of navigation systems, which may include an emitter, which emits energy, such as light, sound, or electromagnetic radiation, and a receiver that detects the energy at a position away from the emitter. This change in energy, from the emitter to the receiver, is used to determine the location of the receiver relative to the emitter. These types of localization systems include conductive, active optical, passive optical, ultrasound, sonic, electromagnetic, etc. An additional representative alternative localization and tracking system is set forth in U.S. Pat. No. 5,983,126, entitled "Catheter Location System and Method," issued Nov. 9, 1999, which is hereby incorporated by reference. Alternatively, the localization system may be a hybrid system that includes components from various systems.

The dynamic reference frame 54 of the electromagnetic tracking system 44 is also coupled to the navigation probe interface 50 to forward the information to the coil array controller 48. The dynamic reference frame 54 is a small magnetic field detector or any other type of detector/transmitter that is designed to be fixed to the patient 14 adjacent to the region being navigated so that any movement of the patient 14 is detected as relative motion between the transmitter coil array 46 and the dynamic reference frame 54. This relative motion is forwarded to the coil array controller 48, which updates registration correlation and maintains accurate navigation, further discussed herein. The dynamic reference frame 54 can be configured as a pair of orthogonally oriented coils, each having the same center or may be configured in any other non-coaxial coil configuration. The dynamic reference frame 54 may be affixed externally to the patient 14, adjacent to the region of navigation, such as the patient's pelvic region, as shown in FIG. 1 or on any other region of the patient. The dynamic reference frame 54 can be affixed to the patient's skin, by way of a stick-on adhesive patch. The dynamic reference frame 54 may also be removably attachable to fiducial markers 60 also positioned on the patient's body and further discussed herein.

Alternatively, the dynamic reference frame 54 may be internally attached, for example, to the pelvis or femur of the patient using bone screws that are attached directly to the bone. This provides increased accuracy since this will track any motion of the bone. Moreover, multiple dynamic reference frames 54 may also be employed to track the position of two bones relative to a joint. For example, one dynamic reference frame 54 may be attached to the pelvis, while a second dynamic reference frame 54 may be attached to the femur during hip arthroplasty. In this way, motion of the femur relative to the pelvis may be detected by the dual dynamic reference frames 54. An exemplary dynamic reference frame 54 and fiducial marker 60, is set forth in U.S. Pat. No. 6,381,485, entitled "Registration of Human Anatomy Integrated for Electromagnetic Localization," issued Apr. 30, 2002, which is hereby incorporated by reference.

Briefly, the navigation system 12 operates as follows. The navigation system 12 creates a translation map between all points in the radiological image generated from the imaging device 16 and the corresponding points in the patient's anatomy in patient space. After this map is established, whenever a tracked instrument 52 is used, the work station 36 in combination with the coil array controller 48 and the C-arm controller 30 uses the translation map to identify the corresponding point on the pre-acquired image, which is displayed on display 10. This identification is known as navigation or localization. An icon representing the localized point or instrument is shown on the display 10, along with five or six degrees of freedom indicia.

To enable navigation, the navigation system 12 must be able to detect both the position of the patient's anatomy 14 and the position of the surgical instrument 52. Knowing the location of these two items allows the navigation system 12 to compute and display the position of the instrument 52 in relation to the patient 14. The tracking system 44 is employed to track the instrument 52 and the anatomy simultaneously. While the display 10 is configured to show the instrument with six degree of freedom accuracy.

The tracking system 44 essentially works by positioning the transmitter coil array 46 adjacent to the patient space to generate a low-energy magnetic field generally referred to as a navigation field. Because every point in the navigation field or patient space is associated with a unique field strength, the electromagnetic tracking system 44 can determine the position of the instrument 52 by measuring the field strength at the sensor 58 location. The dynamic reference frame 54 is fixed to the patient 14 to identify the location of the patient 14 in the navigation field. The electromagnetic tracking system 44 continuously recomputes the relative position of the dynamic reference frame 54 and the instrument 52 during localization and relates this spatial information to patient registration data to enable image guidance of the instrument 52 within the patient 14.

Patient registration is the process of determining how to correlate the position of the instrument 52 on the patient 14 to the position on the diagnostic, pre-acquired, or real-time images. To register the patient 14, the physician or user will select and store particular points from the pre-acquired images and then touch the corresponding points on the patient's anatomy with a pointer probe 62. The navigation system 12 analyzes the relationship between the two sets of points that are selected and computes a match, which correlates every point in the image data with its corresponding point on the patient's anatomy or the patient space. The points that are selected to perform registration are the fiducial arrays or landmarks 60. Again, the landmarks or fiducial points 60 are identifiable on the images and identifiable and accessible on the patient 14. The landmarks 60 can be artificial landmarks 60 that are positioned on the patient 14 or anatomical landmarks 60 that can be easily identified in the image data. The system 12 may also perform 2D to 3D registration by utilizing the acquired 2D images to register 3D volume images by use of contour algorithms, point algorithms or density comparison algorithms, as is known in the art.

In order to maintain registration accuracy, the navigation system 12 continuously tracks the position of the patient 14 during registration and navigation. This is necessary because the patient 14, dynamic reference frame 54, and transmitter coil array 46 may all move during the procedure, even when this movement is not desired. Therefore, if the navigation system 12 did not track the position of the patient 14 or area of the anatomy, any patient movement after image acquisition would result in inaccurate navigation within that image. The dynamic reference frame 54 allows the electromagnetic tracking device 44 to register and track the anatomy. Because the dynamic reference frame 54 is rigidly fixed to the patient 14, any movement of the anatomy or the transmitter coil array 46 is detected as the relative motion between the transmitter coil array 46 and the dynamic reference frame 54. This relative motion is communicated to the coil array controller 48, via the navigation probe interface 50, which updates the registration correlation to thereby maintain accurate navigation.

It should also be understood that localization and registration data may be specific to multiple targets. For example, should a spinal procedure be conducted, each vertebra may be independently tracked and the corresponding image registered to each vertebra. In other words, each vertebra would have its own translation map between all points in the radiological image and the corresponding points in the patient's anatomy in patient space in order to provide a coordinate system for each vertebra being tracked. The tracking system 44 would track any motion in each vertebra by use of a tracking sensor 58 associated with each vertebra. In this way, dual displays 10 may be utilized, further discussed herein, where each display tracks a corresponding vertebra using its corresponding translation map and a surgical implant or instrument 52 may be registered to each vertebra and displayed on the display 10 further assisting an alignment of an implant relative to two articulating or movable bones. Moreover, each separate display in the dual display 10 may superimpose the other vertebra so that it is positioned adjacent to the tracked vertebra thereby adding a further level of information on the six degree of freedom display 10.

As an alternative to using the imaging system 16, in combination with the navigation and tracking system 44, the five or six degree of freedom alignment display 10 can be used in an imageless manner without the imaging system 16. In this regard, the navigation and tracking system 44 may only be employed and the probe 62 may be used to contact or engage various landmarks on the patient. These landmarks can be bony landmarks on the patient, such that upon contacting a number of landmarks for each bone, the workstation 36 can generate a three-dimensional model of the bones. This model is generated based upon the contacts and/or use of atlas maps. The workstation 36 may also generate a center axis of rotation for the joint or planes, based upon the probe contacts. Alternatively, the tracking sensor 58 may be placed on the patient's anatomy and the anatomy moved and correspondingly tracked by the tracking system 44. For example, placing a tracking sensor 58 on the femur and fixing the pelvis in place of a patient and rotating the leg while it is tracked with the tracking system 44 enables the work station 36 to generate a center of axis of the hip joint by use of kinematics and motion analysis algorithms, as is known in the art. If the pelvis is not fixed, another tracking sensor 58 may be placed on the pelvis to identify the center of axis of the hip joint. If a tracking sensor 58 is placed on the femur and a tracking sensor 58 is placed on the tibia, upon moving this portion of the anatomy, a center of axis of the knee joint may be identified. Likewise, by placing a separate tracking sensor 58 on two adjacent vertebra and articulating the spine, the center of axis of the spinal region can also be identified. In this way, a target and/or model based on the center of the particular joint may be designated and identified on the six degree of freedom display 10. Movement of the instrument or implant 52 may then be tracked in relation to this target and/or model to properly align the instrument or implant 52 relative to the target and/or model.

Figure 3A:
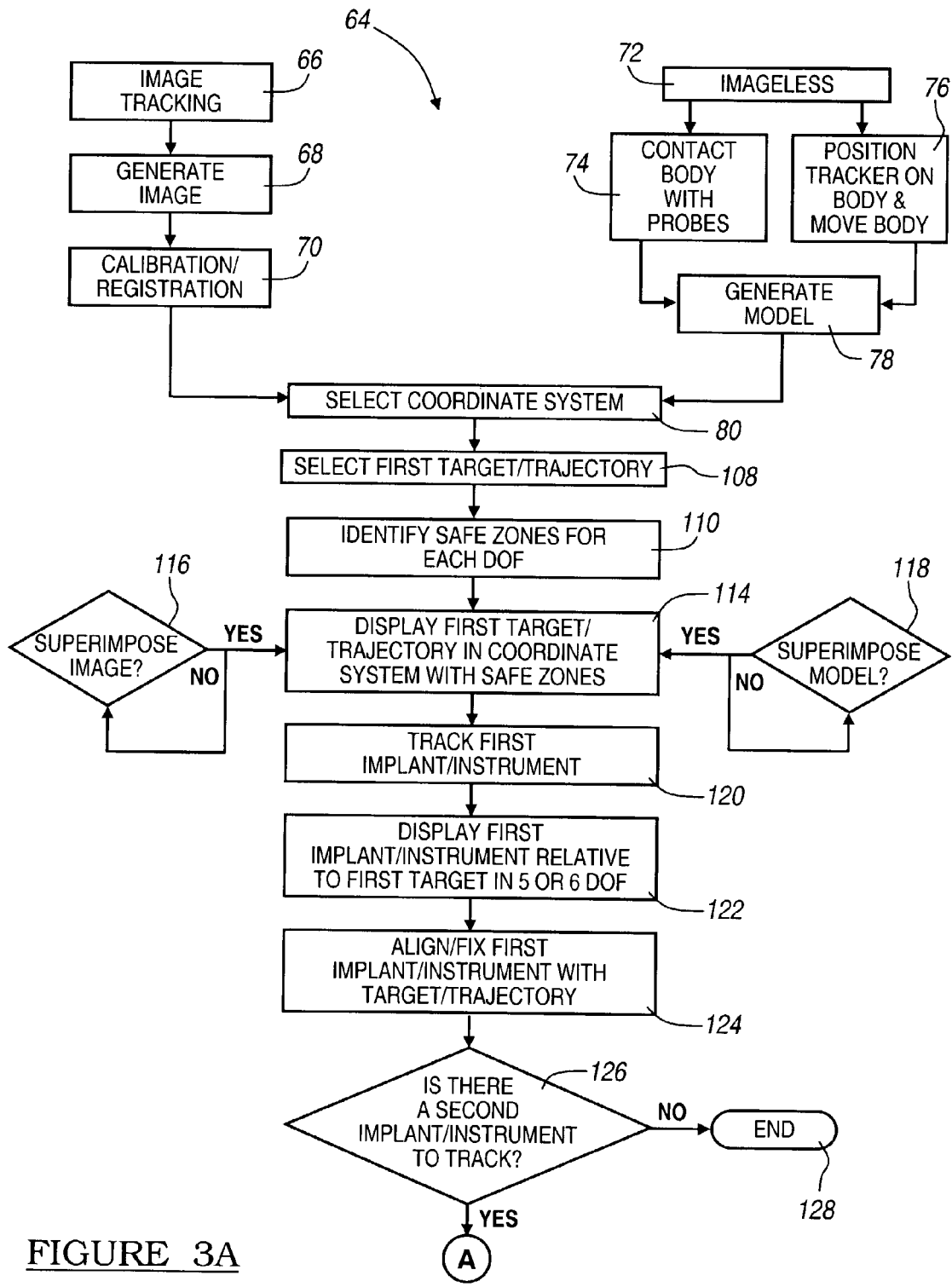
FIGS. 3a and 3b is a logic block diagram illustrating a method for employing the display according to the teachings of the present invention.
Figure 3B:
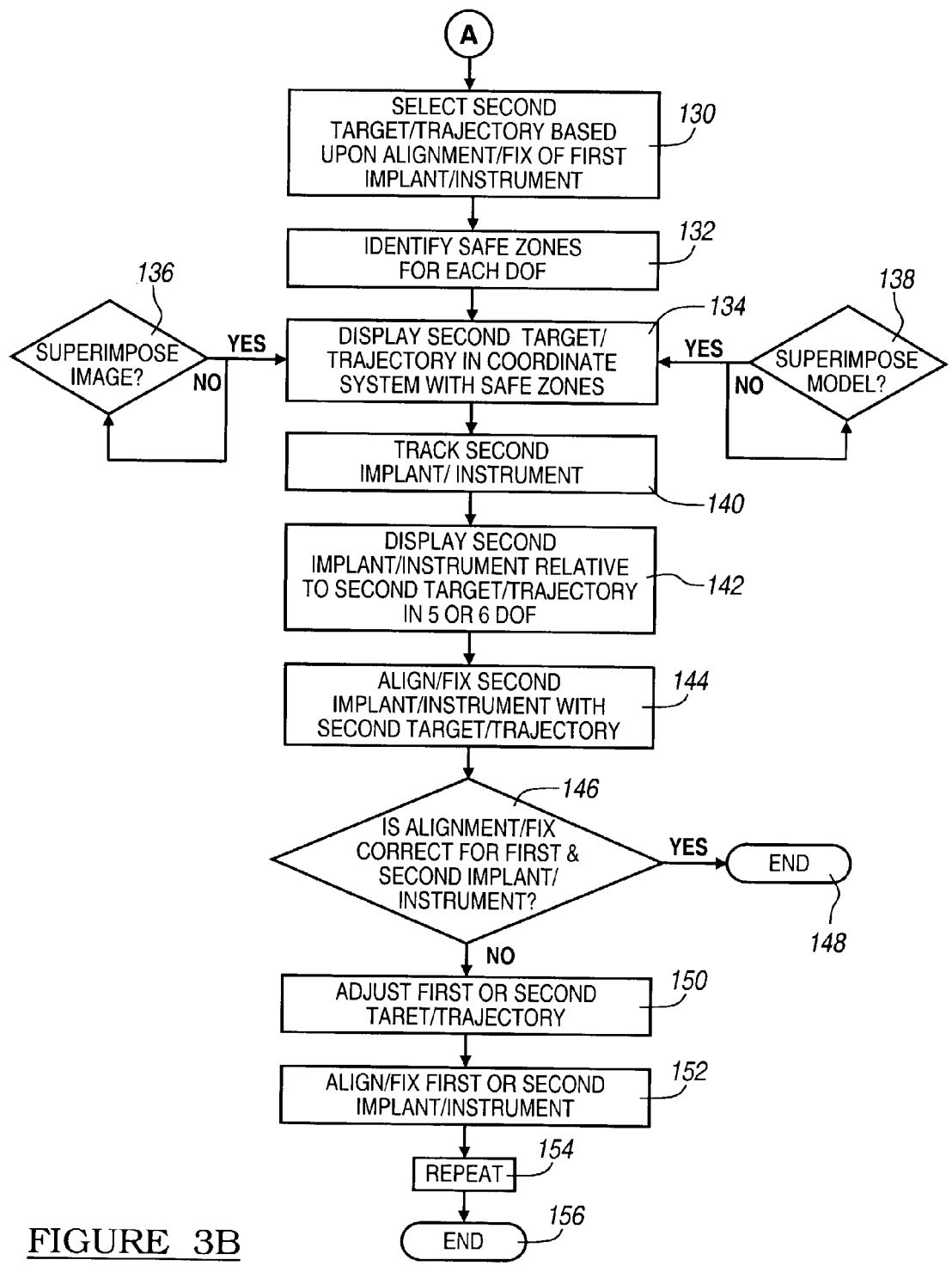

Turning to FIGS. 3*a* and 3*b*, the method of employing the six degree of freedom display 10 is described in further detail. The method 64 begins by determining whether an image based medical procedure will be employed or an image-less medical procedure will be employed. If the image based procedure is being employed, the method proceeds along the first branch. In this regard, when an image based procedure will be utilized, the method begins at block 66 identifying the image tracking procedure. From block 66, the method proceeds to block 68 where images are generated by the imaging system 16. This imaging is performed at the area of interest of the patient 14 by any type of imaging device as previously discussed. Once images have been generated at block 68, the method proceeds to block 70 where calibration and registration is performed. In block 70, calibration of the imaging device 16 takes place using the calibration targets 28. Additionally, registration of the pre-acquired images from block 68 are registered to the patient space of the medical procedure utilizing the fiducial markers 60 and probe 62 as previously discussed. This registration registers the current patient space with the pre-acquired image, so that the instrument 52 or other devices may be tracked during the medical procedure and accurately superimposed over the pre-acquired images generated from the imaging device 16.

If an image-less medical procedure is selected, the method begins at block 72 identifying that an image-less based medical procedure will be performed. This method proceeds to either block 74 identifying a first way to generate image-less models or block 76 identifying a second way to generate image-less models. At block 74, the probe 62 is used to contact the body at various anatomical landmarks in the area of interest, such as a bone. For example, by touching the probe 62 to the pelvis, knee, and ankle, articulation planes can be defined using known algorithms and the center of each joint may also be defined. An example of this type of modeling is set forth in U.S. Pat. No. 5,682,886, which is hereby incorporated by reference. Alternatively, multiple anatomical landmarks can be contacted with the probe 62 to generate a 3-D model with the more points contacted, the more accurate the model depicted.

Secondly, to generate a model at block 76, a tracking device is placed on the body and the body rotated about the joint. When this is done, the plane of rotation and joint center can be identified using known kinematic and/or motion analysis algorithms or using atlas maps or tables, as is known in the art. Once the area of interest has been probed, via block 74 or block 76, a model is generated at block 78. This model can be a 3D surface rendered model, a 2-D model identifying articulating planes or a 3D model identifying articulating planes and rotation, as well as the center of the joints. This enables the display 10 to use the joint centers or articulating planes as the target or trajectory, further discussed herein.

With each of the procedures 74 or 76, the procedure may be initially based on the use of atlas information or a 3-D model that is morphed, to be a patient specific model. In this regard, should the femur be the area of interest, an accurate representation of an ordinary femur may be selected from an atlas map, thereby providing an initial 2-D or 3-D model representing a typical anatomical femur. As with block 74, upon contacting numerous areas on the actual femur with the probe 62, the atlas model may be morphed into a patient specific 3-D model, with the more points contacted, the more accurate the morphed model. Patient specific information may also be acquired using an ultrasound probe to again identify the shape of the patient's natural femur in order to morph the atlas model. A fluoroscopic image of the region may also be used to morph the patient's femur with the atlas model to provide a patient specific morphed model. Proceeding under block 76 and assuming that the area of interest is the hip joint, an atlas model of the femur and pelvis may be the initial starting point. Upon rotating and moving the femur relative to the pelvis, a patient specific morphed model may be created to generate accurate joint centers and axes of motion again using known kinematics and/or motion analysis algorithms Once the image data is calibrated and registered at block 70 or the model is generated at block 78, the method proceeds to block 80. At block 80, the specific type of coordinate system is selected, which will be displayed by indicia on the six degree of freedom display 10. The coordinate systems can be a Cartesian coordinate system, a spherical coordinate system, or a polar coordinate system. By way of example, the Cartesian coordinate system will be selected. The Cartesian coordinate system will include the X, Y, and Z axes, and X rotation, Y rotation, and Z rotation about its respective axes.

Figure 5:
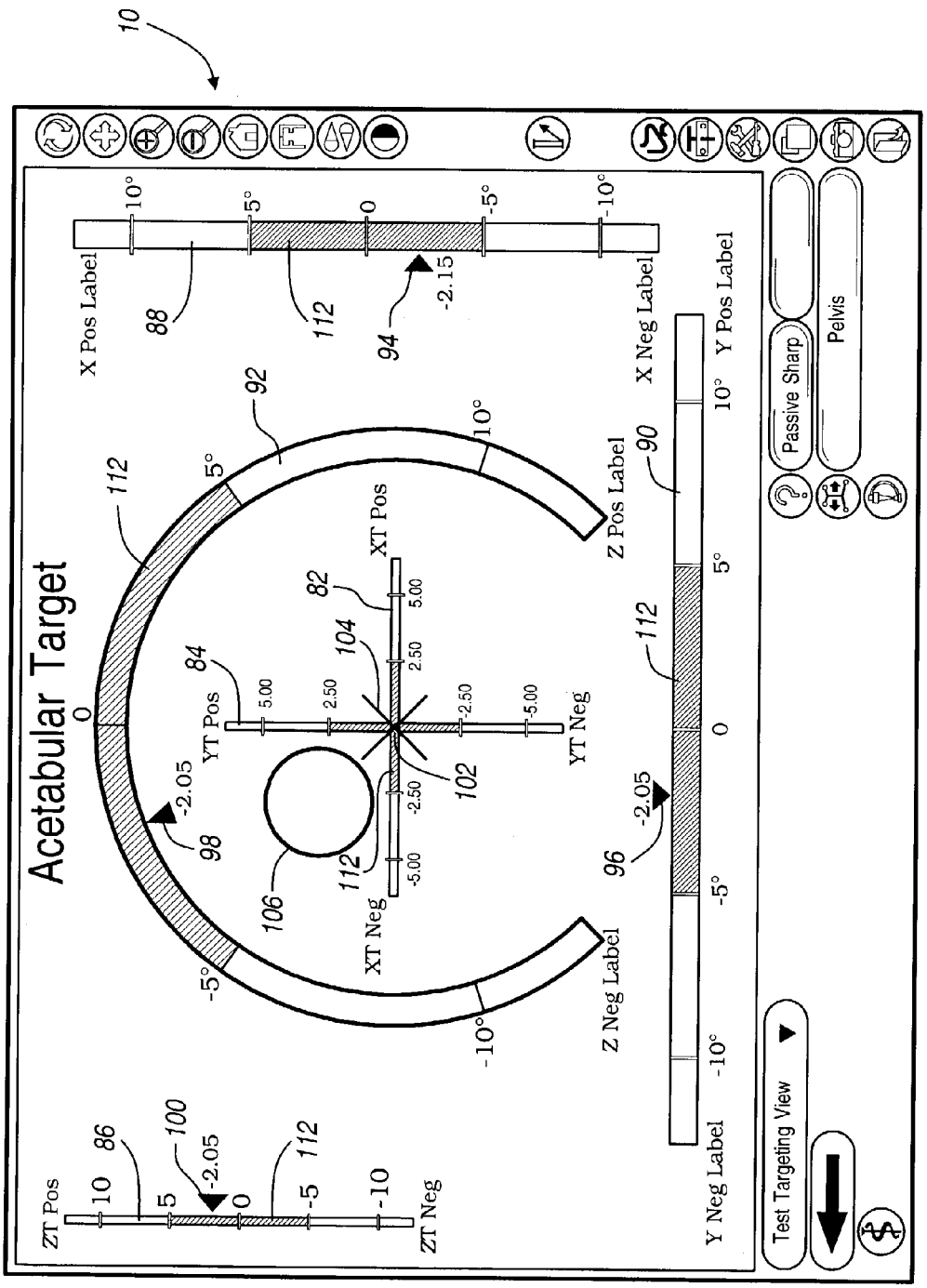
FIG. 5 is a figure of the display according to the teachings of the present invention.

With reference to FIG. 5, the six degree of freedom display 10 is shown in further detail employing the Cartesian coordinate system. In this regard, the X axis 82 and the Y axis 84 are shown positioned on the display 10. The Z axis 86 extends out from the display 10 and is shown in the upper left corner. Rotation about the X axis is shown by bar graph 88 to the right of the display 10 and rotation about the Y axis is shown by bar graph 90 positioned at the bottom of the display 10. Rotation about the Z axis is shown with the arcuate bar graph 92 oriented about the X and Y axes 82 and 84. Each axis, as well as the rotation axes identified by the bar graphs may be color coded to identify safe zones or regions for the item being tracked or navigated. In this regard, the safe zones can be defined as ranges around the planned trajectory path or target where the safe zones are determined by manufactured determined parameters, user determined parameters or patient specific parameter, further discussed herein.

Arrow indicator 94 identifies the degree of rotation about the X axis 82. Arrow indicator 96 shows the amount of rotation about the Y axis 84. Arrow 98 identifies the rotation about the Z axis, while arrow 100 identifies the depth being tracked along the Z axis 86. The origin 102 may be set to be the desired target position or trajectory path. The crosshairs 104 represents the tip of the instrument 52 being tracked, while the circle 106 represents the hind area of the instrument 52 being tracked. With the understanding that the instrument 52 can be any type of medical device or implant. Also, if five degree of freedom information is provided, one of the indicia 82, 84, 86, 88, 90, and 92 will be removed.

Once the coordinate system is selected at block 80, the method proceeds to block 108 where the target or trajectory is selected. The target or trajectory selected at block 108 is typically positioned at the origin 102 on the display 10. In this way, the object being tracked or aligned may be tracked and aligned about the origin 102. Alternatively, the target may be identified at any coordinate within the display 10 or multiple targets may also be identified within the single display 10. An indicia of the target may also be positioned on the display 10. The target is selected based upon the desired area to position the instrument 52 and can be selected from the pre-acquired images or from the 3-D model. Once selected, this target is correlated to the display 10 and generally positioned at the origin 102.

Once the target/trajectory is selected at block 108, such as the origin 102, the method proceeds to block 110 where the safe zones are identified for each degree of freedom. Referring again to FIG. 5, the safe zones 112 are identified for each degree of freedom by color coding. For example, the safe zone 112 for the X axis is between −2.5 and +2.5. The safe zone 112 for rotation about the X axis is between −5° and +5° of rotation about the X axis. The user can simply guide the instrument 52 using the cross hairs 104 and circle 106 to align the instrument 52 within these designated safe zones 112. Again, these safe zones 112 may be determined by manufacture specifications, such as tolerance range of the instruments or positions for implants. The safe zones 112 may also be determined based on the patient, the surgeon conducting the procedure, or any other factors to assist a surgeon in navigating the instrument 52 through the patient 14. These safe zones 112 may also be identified via an audible signal or tone or a varying tone. The safe zones 112 may also be identified by any other convenient manner to be set out on the display 10.

Figure 6:
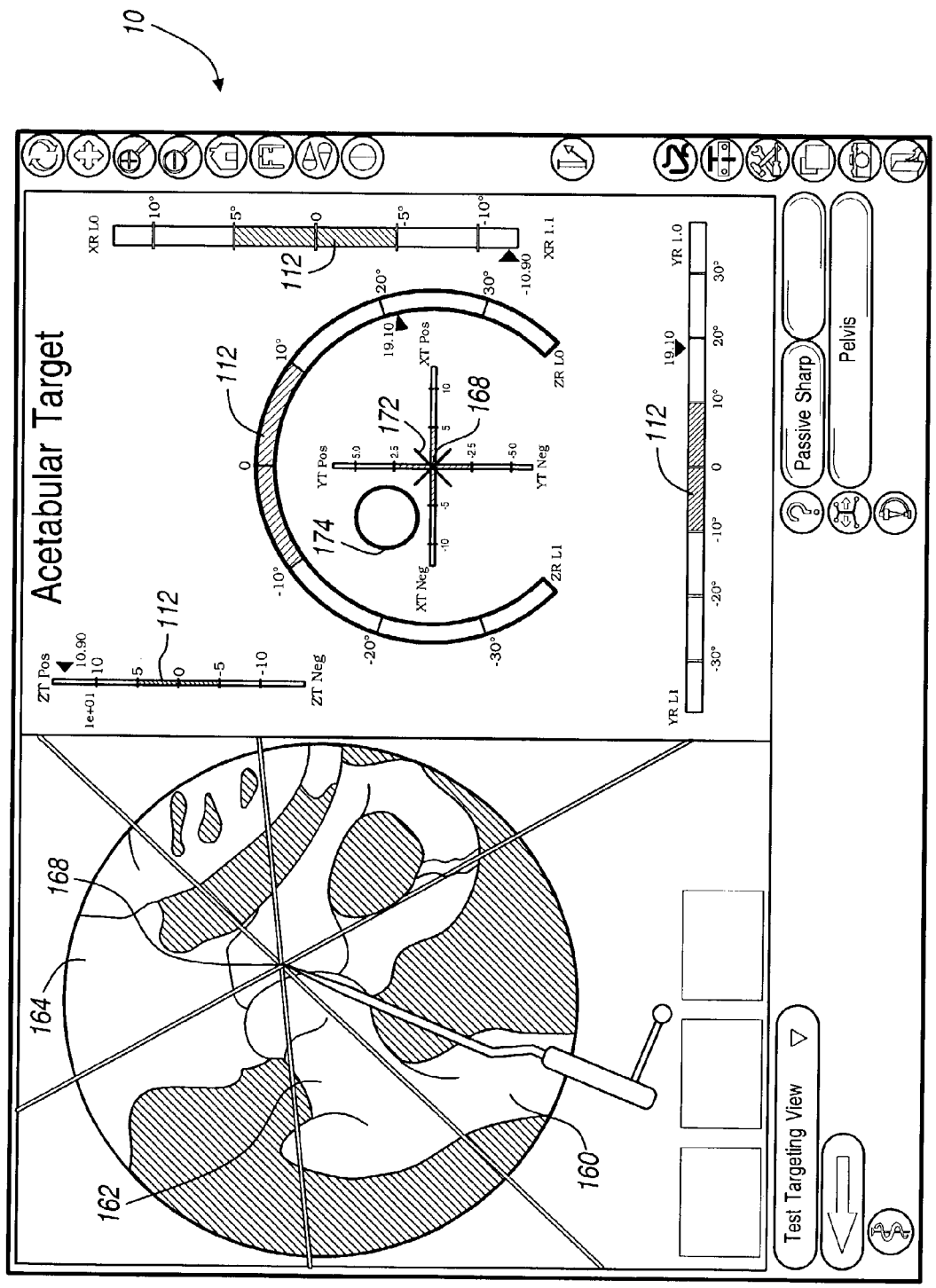
FIG. 6 is a split screen view of the display according to the teachings of the present invention.

Once the safe zones 112 are identified for each degree of freedom in block 110, the method proceeds to block 114 where the target trajectory in the selected coordinate system is displayed with the safe zones 112, as shown in FIG. 5. At block 116, if an image based method is being conducted, a decision whether to superimpose the image over the target/trajectory is made. Alternatively, the image may be placed adjacent to the target trajectory display, as is shown in FIG. 6, and further discussed herein. Should the image-less based medical procedure be conducted, at block 118, a determination is made whether to superimpose the model that was generated at block 78. Here again, this model may be superimposed over the target/trajectory display on display 10 or may be positioned adjacent to the target/trajectory display in a split screen or on a separate display.

Once the target/trajectory 102 is displayed along with the safe zones 112 in the proper coordinate system, as shown in FIG. 5, the method proceeds to block 120 where the first implant/instrument 52 is tracked with the navigation system 44. With the implant/instrument 52 being tracked at block 120, the method proceeds to block 122 wherein indicia representing the implant/instrument 52 is displayed on the display 10, with either five or six degrees of freedom information. Here again, referring to FIG. 5, the indicia representing the implant/instrument 52 is the crosshairs 104 and the circle 106 designating the tip and hind, respectively. The tip 104 and hind 106 is represented in relation to the target/trajectory path 102 in six degrees of freedom. This six degrees of freedom include the X and Y locations, as well as the depth Z of the implant/instrument 52 displayed. In addition, the rotation about each of the axes is also provided. This rotation can be helpful in many applications, including orthopedic, where rotation specific components need to be positioned relative to one another. For example, in a spinal application, alignment of a pedicle screw in relation to a spinal rod, would require information regarding the rotation of the screw relative to the rod. In cardiac procedures, this may be useful where ablation is necessary on a certain side of an artery and the ablation electrode is only positioned on one side of the catheter. In this situation, rotation of the catheter relative to the target in the artery is critical. In a neuro procedure, a biopsy needle may only have a biopsy port positioned upon one portion of the circumference of the needle, thereby requiring the rotation of the biopsy needle to be known in order to provide the proper capture of the relevant biopsy sample. Without this display, this information would not be available.

With the indicia of the implant/instrument 52 being displayed, the implant/instrument 52 is aligned or fixed with the target/trajectory 102 at block 124. In this regard, the tip 104 and the hind 106 are aligned and fixed relative to the target/trajectory 102 at the origin and the rotational orientation is also aligned to the desired position. Again, the target/trajectory 102 may not be positioned at the origin and can be positioned anywhere within the coordinate system if desired. As shown in FIG. 5, the tip 104 of the implant/instrument 52 is shown aligned with the target 102, while the hind 106 is slightly offset from the target/trajectory 102. Once the implant/instrument 52 is aligned and fixed relative to the target/trajectory 102, the method proceeds to block 126.

At block 126, a determination is made as to whether there is a second implant/instrument 52 to be tracked. If there is not a second implant/instrument 52 to be tracked, the method ends at block 128. Should there be a second implant/instrument 52 to track, such as a corresponding implant component that articulates with the first implant, the method proceeds to block 130. At block 130, a second target/trajectory 102 is selected, which is based upon the alignment or fixation of the first implant/instrument 52 relative to the first target/trajectory 102. In this regard, if the surgeon is not able to position the first implant/instrument 52 at the desired target/trajectory 102, this offset from the target/trajectory 102 may affect the second implant, which possibly articulates or mates with the first implant. If this is the case, the second target/trajectory 102 will need to take into consideration this offset in order to provide proper articulation and alignment of the first implant component with the second implant component.

With minimally invasive types of procedures, the implant may also have numerous components with each component articulating or mating with another component, thereby requiring tracking of each component as it is implanted during the minimally invasive procedure. This second target/trajectory 102 may be displayed on a separate display 10 (see FIG. 1), positioned via a split screen of a single display 10 or may be superimposed upon the existing display that displays the first target 102 and implant position. In this way, orientation and placement of both the first and second implants, which are dependent upon one another can be shown in the display 10 providing the surgeon the opportunity to adjust either position of either implant intraoperatively before the implants are permanently affixed to the patient 14. These types of implants include knee implants, hip implants, shoulder implants, spinal implants, or any other type of implant, which has a bearing surface and an articulating surface or any type of implant having multiple mating and connecting components.

Once the second target/trajectory 102 has been selected at block 130, the method proceeds to block 132. At block 132, the safe zones 112 for each degree of freedom is selected for the second implant/instrument 52 similar to the way the first set of safe zones 112 were selected for the first implant/instrument 52. Once the second safe zones 112 are selected, the method proceeds to block 134. At block 134, the display 10 displays the second target/trajectory 102 in the same coordinate system with the second safe zones 112. Here again, at block 136, if it is an image based medical procedure, the pre-acquired image may be superimposed on to the target/trajectory 102. Alternatively, this image can be positioned adjacent the target screen in a split screen configuration (see FIGS. 6 and 7). If the method is proceeding as an image-less type medical procedure, at block 138, decision is made whether to superimpose the generated model from block 78. Once the target/trajectory 102 is in the proper coordinate system with the safe zone 112 are displayed at display 10, the surgical implant/instrument 52 is tracked at block 140. Here again, the second implant/instrument 52 can be tracked on a separate display 10 or be tracked on the same display as the first implant/instrument 52.

Alternatively, separate displays 10 may be used where information is linked between the displays showing the second implant/instrument 52 in relation to the first implant/instrument 52. With the second implant/instrument 52 being tracked at block 140, the second implant/instrument 52 is displayed in relation to the second target/trajectory 102 in five or six degrees of freedom at block 142. Again, this may be a separate display 10, a split screen display 10 with both the first target/trajectory 102 and the second target/trajectory 102 or the same display 10 displaying both targets/trajectories 102. While the second implant/instrument 52 is being displayed, the second implant/instrument 52 is aligned and fixed at the second target/trajectory 102 at block 144. Once the second implant/instrument 52 is fixed at block 144, the method proceeds to block 146.

At block 146, a determination is made whether the alignment or fixation of the first and second implants/instruments 52 are correct. In this regard, with two separate displays 10 linked or with a single display 10, showing both targets/trajectories 102, a surgeon can determine whether each implant/instrument 52 is within its desired safe zones 112 and, therefore, optimally positioned for proper articulation. Here again, these safe zones 112 may be color coded for the different safe zones provided. If both implants are positioned and fixed at the proper targets, the method ends at block 148. If one or both of the implants are not properly positioned, adjustment of the first or second target/trajectory 102 is performed at block 150. Once either or both targets are adjusted, realignment of the first and/or second implants/instruments 52 are performed at block 152. Here again, since multiple component implants are dependent upon one another with respect to their position and orientation, alignment and adjustments of the targets/trajectories 102 may be performed several times until the optimum placement for each is performed at repeat block 154. Thereafter, the method terminates at end block 156.

While the above-identified procedure is discussed in relation to an orthopedic medical procedure in which an implant having multiple implant components is implanted within a patient using the six degree of freedom display 10, it should be noted that the six degree of freedom display 10 may be used to track other medical devices as well. For example, as was briefly discussed, an ablation catheter generally has an electrode positioned only on one angular portion of its circumference. Likewise, the wall of an artery typically has a larger plaque build-up on one side. Therefore, it is desirable to align that ablation electrode with the proper side of the artery wall during the procedure. With the six degree of freedom display 10, the surgeon can easily identify the location, depth and angular rotation of the catheter relative to the artery wall. Other types of procedures may require the medical instrument or probe to be properly oriented and located within the patient, such as identifying and tracking tumors, soft tissue, etc. By knowing and displaying the six degree of freedom movement of the medical device on the display 10, the medical procedure is optimized.

It should also be pointed out that the method discussed above requires that the implant/instrument 52 have a tracking sensor associated therewith in order to identify the location of the tracked device in six degrees of freedom and display it on the display 10. The tracking sensors may be attached directly to implants, attached to the instruments that engage the implants or attach to members extending out from the implants. These tracking sensors again may be electromagnetic tracking sensors, optical tracking sensors, acoustic tracking sensors, etc. Examples of various targets, which may or may not be superimposed on the display again include orthopedic targets, spinal targets, cardiovascular targets, neurovascular targets, soft tissue targets, etc. Specific examples include again the location of the plaque on a wall of an artery, the center of an articulating joint being replaced, the center of the implant placement, etc. By displaying two targets, either on separate displays or on the same display, the surgeon can dynamically plan and trial implant placements by moving one component of the implant to see where the other articulating component of the implant should be positioned. In this way, the surgeon can trial the implant confirming its placement and orientation, via the display 10 before the implant is permanently affixed to the patient 14.

In a spinal procedure, two adjacent vertebra bodies can be tracked and displayed on two separate displays. In this way, if a single jig, such as a cutting jig is used to cut both the surface of the first vertebra and the surface of the second vertebra, orientation of the jig may be displayed on each separate display in relation to the corresponding vertebra being acted upon, thereby enabling simultaneous tracking of the two planes being resected for each separate vertebra on a dual display system. Additionally, each vertebra may be displayed on each of the dual displays so that the vertebra being tracked is shown with the adjacent vertebra superimposed adjacent thereto. Once the vertebra bodies are prepared, the implant is typically placed between each vertebra on the prepared site. Other ways of preparing this site is by using drills, reamers, burrs, trephines or any other appropriate cutting or milling device.

Briefly, the method, as shown in FIGS. 3a and 3b, demonstrates that the display 10 illustrated both the position and orientation of an object with respect to a desired position and orientation with six degrees of freedom accuracy. The display 10 may be automatically updated in real-time using the navigation system 44 to report the orientation of the tracked device. The user may also adjust the display 10 in order to control a device's orientation. The display 10 again consists of three rotational indicators (RX, RY, RZ) and three translational indicators or indicia (TX, TY, TZ). Each indicator shows both visual and quantitative information about the orientation of the device. Each indicator also displays a predetermined safe zone 112 and application-specific label for each degree of freedom. As noted, it may also be relevant to overlay the display 10 over anatomical image data from the imaging device 16. When working with 3-D image data sets, the anatomy normal to the tip 104 of the positioned device can provide the user with additional positional information.

Tones, labels, colors, shading, overlaying with image data can all be modified and incorporated into the display 10. The current display 10 is also shown as a Cartesian coordinate based display, but again could be based on a polar based display or a spherical based display and a quick switch between both can be supplied or simultaneously displayed. The display can also be configured by the user to hide parameters, location, size, colors, labels, etc.

Some medical applications that may be commonly displayed and linked to the display 10 are: 1) reaming of an acetabular cup with major focus upon RY and RZ, 2) length of leg during hip and knee procedures focused upon TZ and RZ, 3) biopsies and ablations focused upon RX, RY, and RZ for direction of the therapy device, and 4) catheters with side ports for sensing information or delivery of devices, therapies, drugs, stem cells, etc. focused upon six degree of freedom information.

Figure 4B:
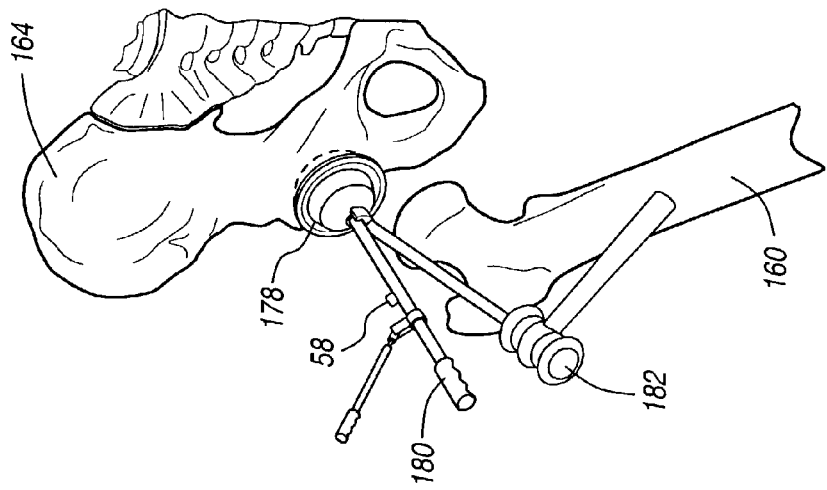
FIGS. 4a-4e illustrate a medical procedure employing the display according to the teachings of the present invention.
Figure 4A:
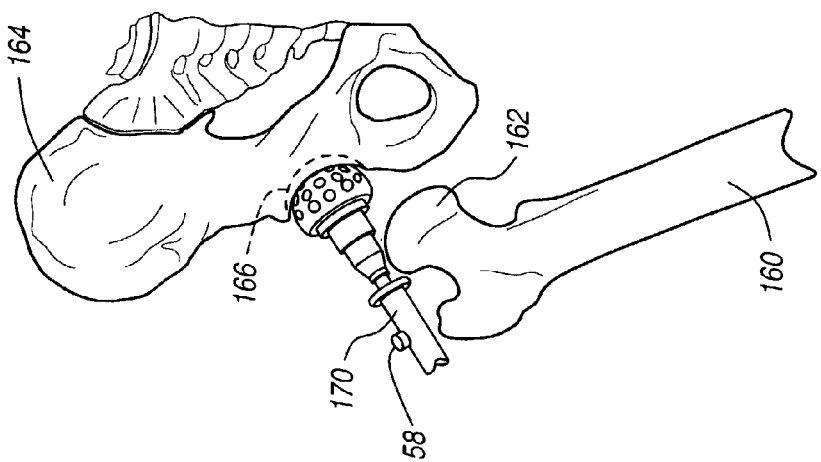
Figure 4E:
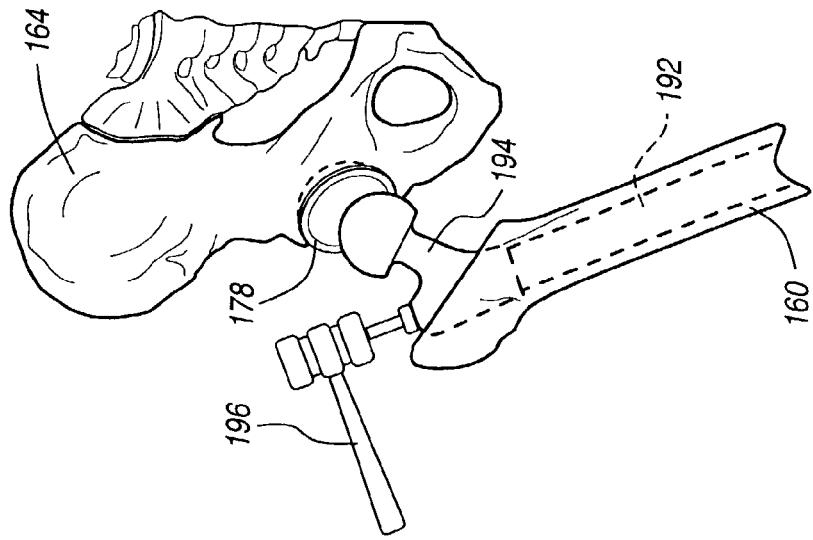

Referring now to FIGS. 4a-4e, a medical procedure employing a six degree of freedom alignment display 10 is shown in further detail. In this example, an orthopedic medical procedure replacing the hip joint is illustrated. During this procedure, various instruments 52, as well as the implants 52 are tracked and aligned using the six degree of freedom display 10. Referring specifically to FIG. 4a, a femur 160 having a femoral head 162 is illustrated, along with a pelvis 164 having an acetabulum 166. Assuming that the medical procedure being performed is an image based system, this area of interest will be imaged by the imaging device 16. Here again, the dynamic reference frame 54 may be attached to the femur 154 or the pelvis 164 or two dynamic frames 54 may be attached, one to each bone to provide additional accuracy during the medical procedure. With the head 162 dislocated from the acetabulum 166, a center of articulation of the acetabulum 166 is identified as the target 168, shown in FIG. 6.

In this regard, FIG. 6 illustrates the display 10 configured as a split screen with the right identifying the six degree of freedom display and the left illustrating the pre-acquired image with the center of articulation 168 being the intersection of the X, Y, and Z axes. As illustrated in FIG. 4a, a reamer 170 having a tracking sensor 58 is shown reaming the acetabulum 166. The tracking system 44 is able to accurately identify the navigation of the tip and hind of the reamer 170. As illustrated in FIG. 6, in the right half of the split screen, one can observe that the tip represented by the crosshairs 172 is properly positioned along the X and Y coordinates and within the corresponding safe zones 112, however, the hind portion of the instrument 170, as identified by the circle 174, is angularly offset from the target 168 at the origin. The surgeon can then angularly adjust the hind portion 174 of the instrument 170 until the hind portion 174 is shown in the display 10 as positioned over the crosshairs 172, thereby assuring proper alignment of the reaming device 170 for subsequent proper placement of the acetabular cup implant. By tracking the reamer 170, the surgeon can be relatively confident that an acetabular cup implant will be properly positioned before the implant is even impacted into the acetabulum 166.

Figure 7:
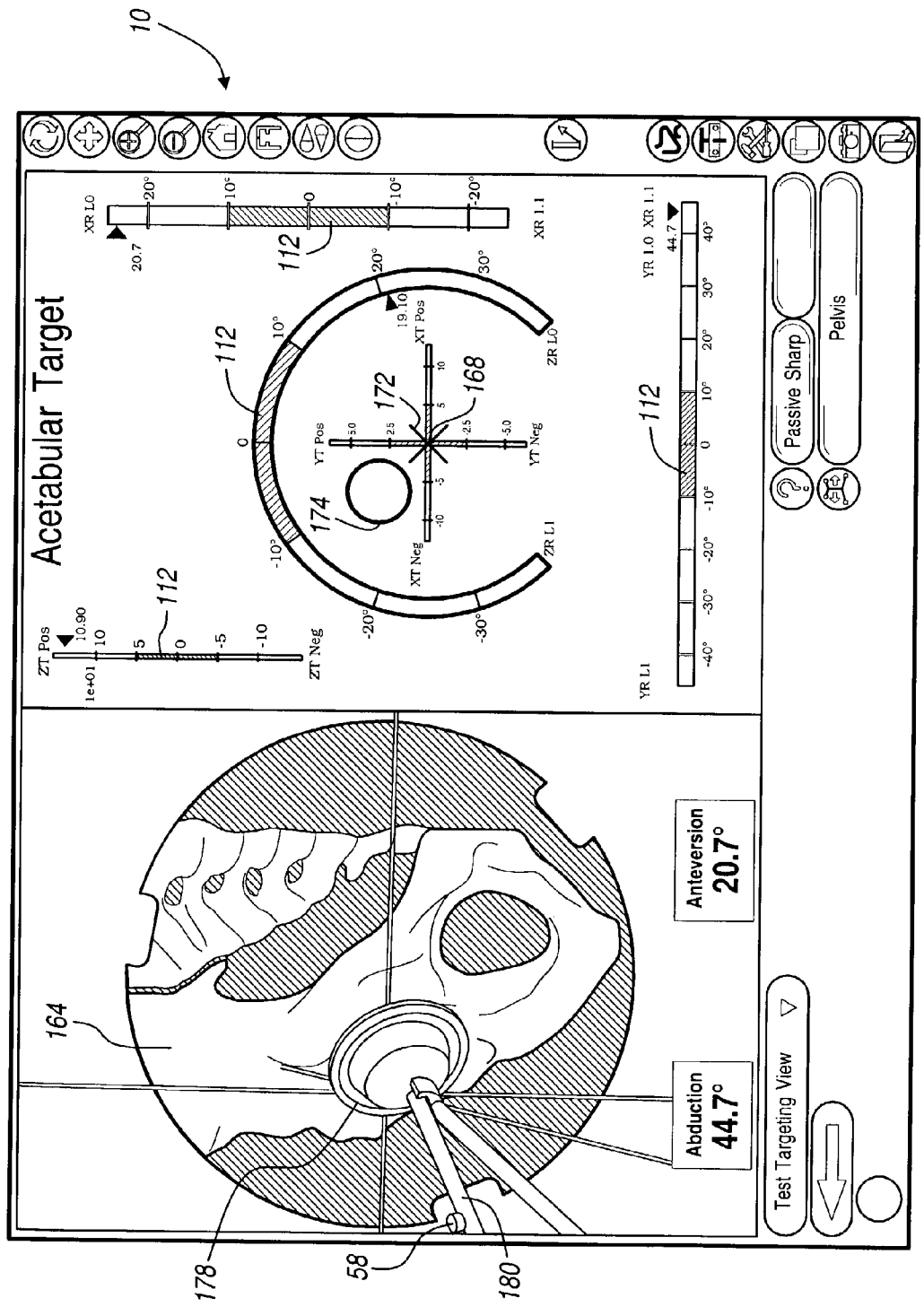
FIG. 7 is an additional split screen view of the display according to the teachings of the present invention.

Turning to FIG. 4b, an acetabular cup 178 is shown being impacted into the reamed acetabulum 166, via the tracked guide tool 180 with an impactor 182. The guide tool 180 has a distal end, which is nestingly received within the acetabular cup 178. Thus, by tracking the instrument 180, via tracking sensor 58, orientation of the acetabular cup 178 may be displayed on the display 10 in six degrees of freedom. In this way, before the acetabular cup 178 is impacted into the acetabulum 166, the surgeon can view on the display 10 whether the acetabular cup 178 is properly positioned at the proper angular orientation, as shown in FIG. 7, the impactor 180 is shown superimposed over an image generated by the imaging device 16. In this way, the proper orientation, including abduction and anteversion is achieved before the acetabular cup 178 is permanently implanted.

Once the acetabular cup 178 has been impacted, the femoral head 162 is resected along a plane 184 by use of a cutting guide 186, having the tracking sensor 58 and a saw blade 188. By using the center of the femoral head 162 as the second target, the cutting plane 184 may be properly defined to provide proper articulation with the acetabular cup 178 before a hip stem is implanted in the femur 160. Here again, the second target is dependent upon the first target. Thus, if the acetabular cup 178 was implanted somewhat offset from its target, the second target may be properly compensated to accommodate for this offset by use of the display 10. In this regard, a second display illustrating the target for the cutting plane 184 may be provided.

Figure 4D:
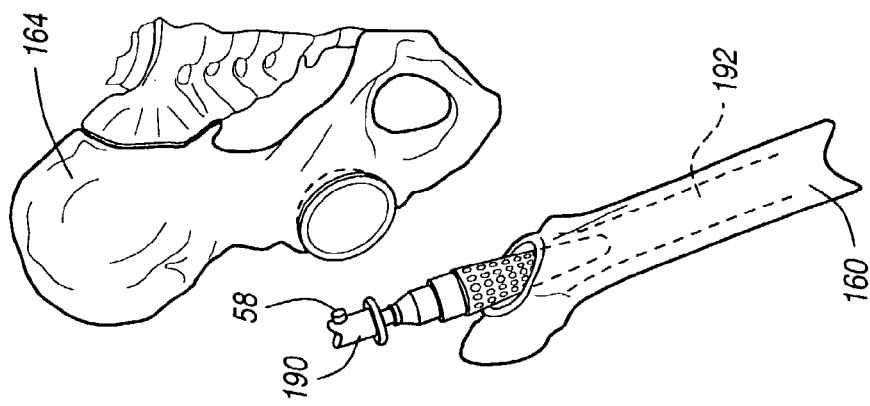
Figure 4C:
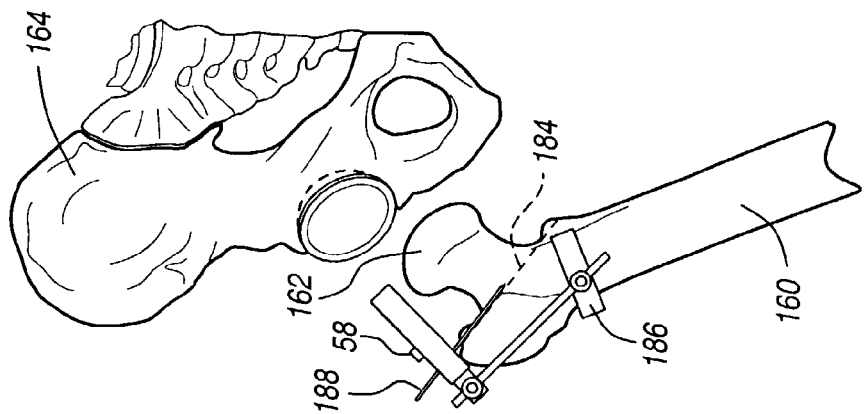

Once the femoral head 162 of the femur 160 has been resected, as shown in FIG. 4d, a reamer 190 is employed to ream out the intramedullary canal 192 of the femur 160. In order to provide proper angular orientation of the reamer 190, as well as the depth, a subsequent target can be defined and identified on the display 10 and tracked by use of the tracking sensor 58. This target may be displayed separately or in combination with the previously acquired targets. By insuring the proper angle of the reamer 190 relative to the longitudinal axis of the femur 160 is tracked and displayed on display 10, the surgeon can be provided a higher level of confidence that the hip stem will be properly positioned within the intramedullary canal 192.

Once the intramedullary canal 192 has been reamed by the reamer 190, a hip stem 194 is impacted with an impactor 196 into the intramedullary canal 192. By targeting the acetabular cup location, along with the resection plane 184 and the reaming axis of the reamer 190, upon positioning the hip stem 194, within the femur 160, proper articulation and range of motion between the acetabular cup 178 and the hip stem 194 is achieved without time consuming trialing as is conducted in conventional orthopedic procedures. Thus, by providing the safe zones 112 in relation to the hip stem 194 size, proper articulation with the acetabular cup 178 is achieved. Here again, while an example of an orthopedic hip replacement is set out, the six degree of freedom display 10 may be utilized with any type of medical procedure requiring visualization of a medical device with six degree freedom information.

The six degree of freedom display 10 enables implants, devices and therapies that have a specific orientation relative to the patient anatomy 14 to be properly positioned by use of the display 10. As was noted, it is difficult to visualize the correct placement of devices that require five or six degree of freedom alignment. Also, the orientation of multiple-segment implants, devices, or therapies in five and six degrees of freedom so that they are placed or activated in the correct orientation to one another is achieved with the display 10. Since the location and orientation is dependent upon one another to be effective, by having the proper orientation, improved life of the implants, the proper degrees of motion, and patient outcome is enhanced. Also, the six degree of freedom display 10 may be used as a user input mechanism by way of keyboard 38 for controlling each degree of freedom of a surgical robotic device. In this regard, the user can input controls with the joystick, touch screen or keyboard 38 to control a robotic device. These devices also include drill guide holders, drill holders, mechanically adjusted or line devices, such as orthopedic cutting blocks, or can be used to control and drive the alignment of the imaging system 16, or any other type of imaging system.

Since multiple implants and therapies, or multi-segment/compartment implants require multiple alignments, the display 10 may include a stereo display or two displays 10. These displays may or may not be linked, depending on the certain procedure. The target point/location (translation and orientation of each implant component is dependent upon the other implant placement or location). Therefore, the adjustment or dynamic targeting of the dependent implant needs to be input to the dependent implant and visually displayed. Again, this can be done by two separate displays or by superimposing multiple targets on a single display. Many implants such as spinal disc implants, total knee and total hip replacements repair patient anatomy 14 by replacing the anatomy (bone, etc.) and restoring the patient 14 to the original biomechanics, size and kinematics. The benefit of the six degree of freedom alignment display 10 is that original patient data, such as the images can be entered, manually or collectively, via the imaging device 16 or image-less system used for placement of the implant. Again, manually, the user can enter data, overlay templates, or collect data, via the imaging system 16. An example, as discussed herein of an application is the alignment of a femoral neck of a hip implant in the previous patient alignment. The previous patient alignment can be acquired by landmarking the patient femoral head by using biomechanics to determine the center and alignment of the current line and angle of the femoral head. This information can be used as the target on the display 10 in order to properly align the implant replacing the femoral head.

The six degree of freedom display 10 also provides orientation guidance on a single display. Separate visual and quantitative read-outs for each degree of freedom is also displayed on the display 10. Visual representations or indicia of procedure-specific accepted values (i.e., a "safe zone 112") for each degree of freedom is also clearly displayed on the display 10. These safe zones 112 are displayed as specifics or ranges for the user to align or place within. The procedure specific accepted values for the safe zones 112 can be manufacture determined, user determined, patient specific (calculated) or determined from algorithms (finite element analysis, kinematics, etc. atlas or tables). It can also be fixed or configurable. Safe zones 112 can also be defined as ranges around a planned trajectory path or the specific trajectory path itself (range zero). The trajectory paths are input as selected points by the user or paths defined from the patient image data (segmented vascular structure, calculated centers of bone/joints, anatomical path calculated by known computed methods, etc.).

Figure 8A:
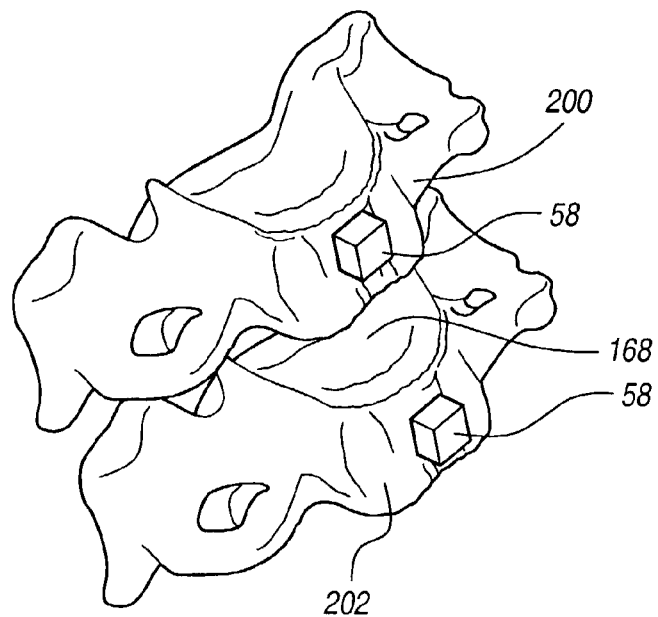
FIGS. 8a-8g illustrate another medical procedure employing the display according to the teachings of the present invention.
Figure 8B:
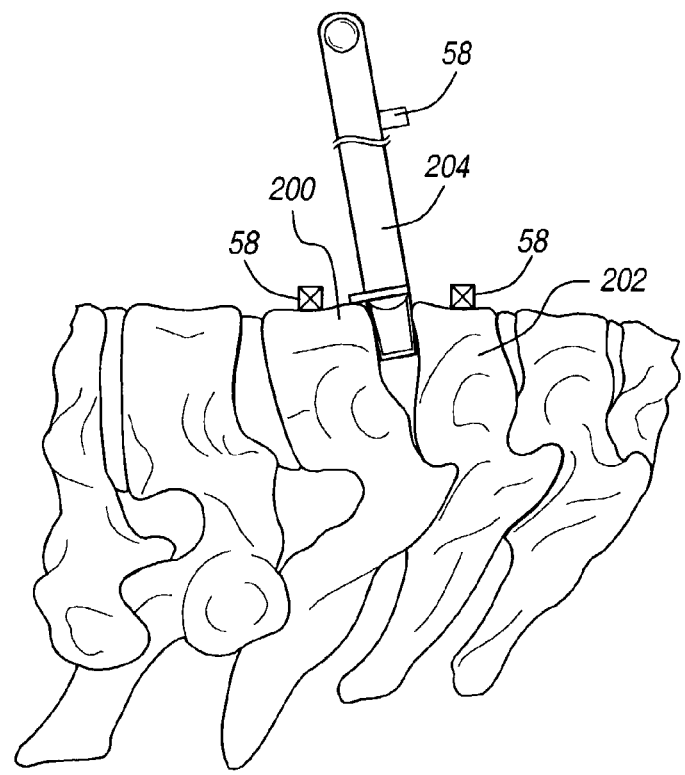
Figure 8C:
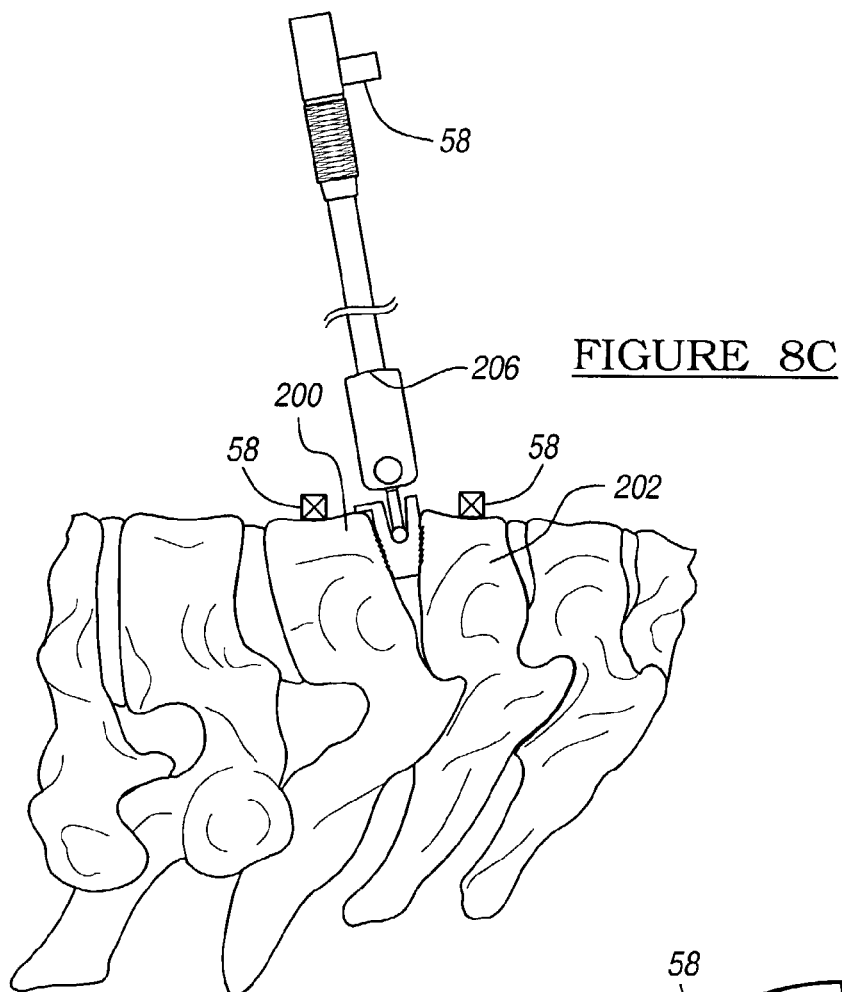
Figure 8D:
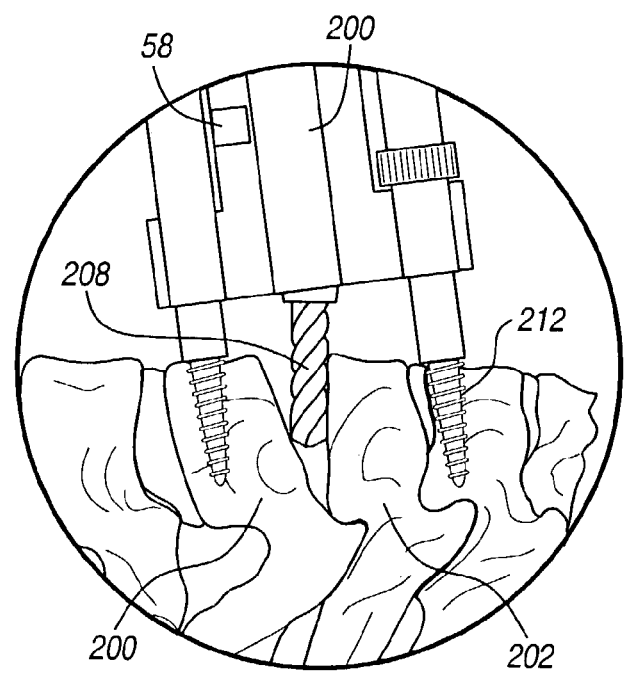
Figure 8E:
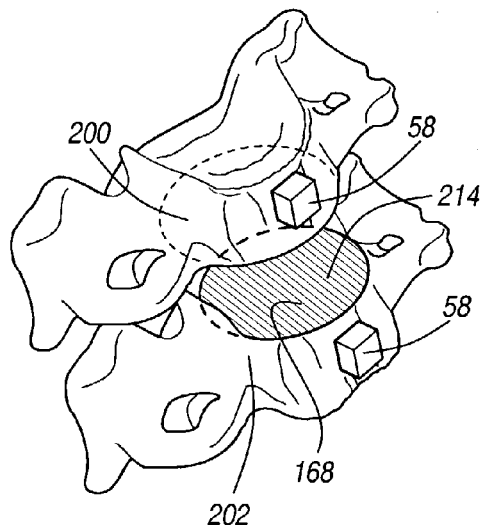
Figure 8F:
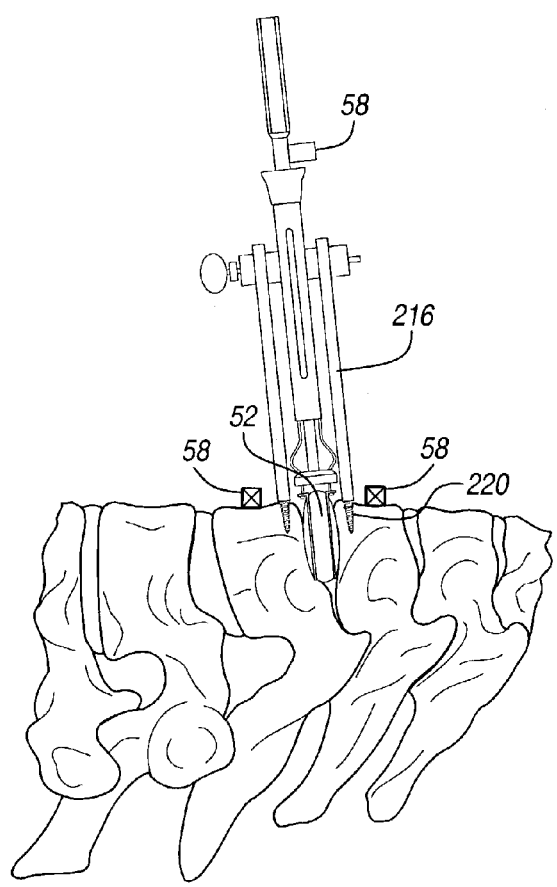
Figure 8G:
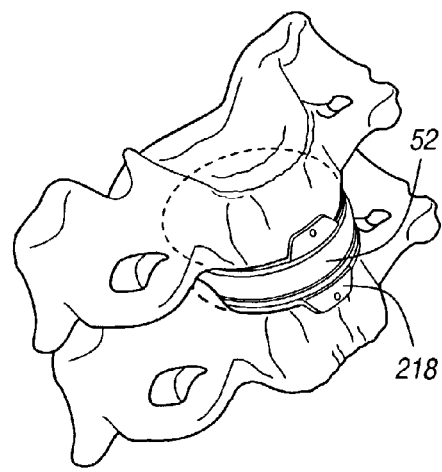
Figure 9:
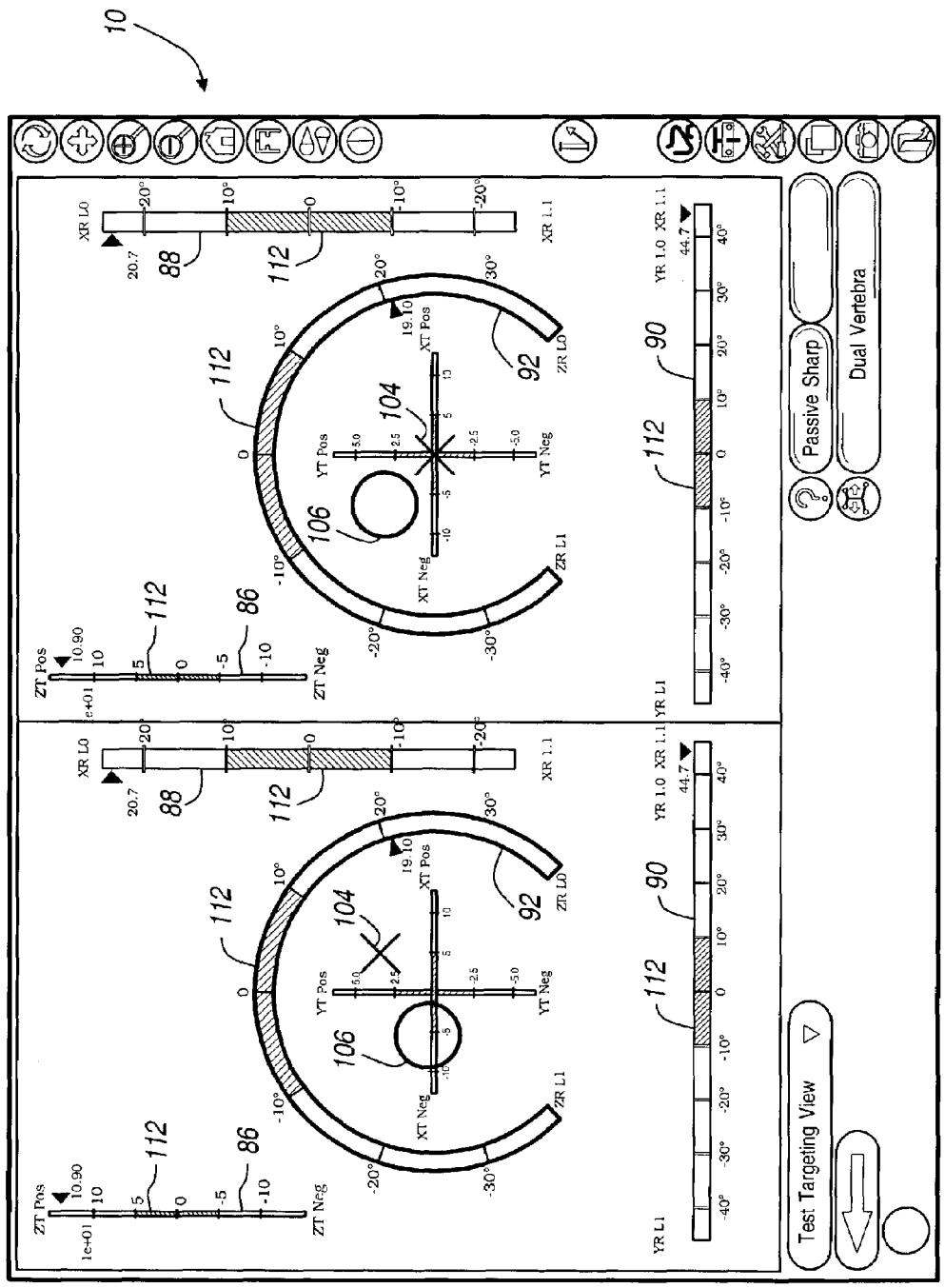
FIG. 9 is an illustration of a dual display according to the teachings of the present invention.

Turning now to FIGS. 8a-8g, another medical procedure employing the six degree of freedom alignment display 10 is shown in further detail, along with FIG. 9 illustrating the use of the display 10 during this medical procedure. In this example, a spinal medical procedure that implants a cervical disc implant between two vertebrae is illustrated. During this procedure, various instruments 52, as well as the implant 52 are tracked and aligned using the six degree of freedom display 10. Also, the bony structures during the procedure are also tracked.

Referring specifically to FIG. 8a, a first vertebra or vertebral body 200 is shown positioned adjacent to a second vertebra or vertebral body 202 in the cervical area of the spine. Assuming that the medical procedure is being performed in an image based system, this area of interest would be imaged by the imaging device 16. Again, a dynamic reference frame 54 may be attached to the first vertebra 200 and a second dynamic reference frame 54 may be attached to the second vertebra 202. These dynamic reference frames 54 may also be combined with tracking sensors 58, which are shown attached to the vertebral bodies 200 and 202. A center of articulation of the vertebra 200 and a center of articulation of a vertebra 202 may be identified as the targets 168 on the dual display illustrated on FIG. 9. In this way, by utilizing the center of articulation of each vertebral body with respect to each other as the targets 168, tracking of the instruments 52 used during the procedure, as well as the implant 52 with respect to these articulation centers may be achieved.

Referring to FIG. 8b, a cam distracter instrument 204 is shown distracting the vertebra 200 relative to the vertebra 202. The cam distracter 204 may be tracked, via another tracking sensor 58 affixed to the cam distracter 204. In this way, the six degree of freedom display 10 illustrated in FIG. 9 can illustrate a location of the cam distracter 204 relative to the center of each vertebra 200 and 202 independently on the display. Since the instrument 204 is rigid, by locating the tracking sensor 58 on the instrument 204, the distal end of the instrument 204 is known and may be illustrated on the display 10 using crosshairs 104 and circle 106 to represent the tip and hind, respectively.

Once each vertebrae 200 and 202 have been distracted by the cam distracter 204, a sagittal wedge 206 also having a tracking sensor 58 is utilized and shown in FIG. 8c. The sagittal wedge 206 is used to center each vertebrae 200 and 202, along the sagittal plane and again may be tracked and displayed with six degree of freedom on the display 10, as illustrated in FIG. 9. In this regard, the surgeon can confirm both visually and via the display 10 that the sagittal wedge 206 is centered on the sagittal plane between the vertebrae 200 and 202, as well as obtain the proper depth, via the Z axis display 86 on the display 10, illustrated in FIG. 9.

Once the sagittal centering has been achieved with the sagittal wedge 206, the medical procedure proceeds to burring as shown in FIG. 8d. In this regard, a burr 208 attached to a burring hand piece 210, also having a tracking sensor 58, is used to burr an area between the first vertebra 200 and the second vertebra 202. Here again, the orientation of the burr 208 relative to each vertebrae 200 and 202 may be displayed on the display 10 with six degree of freedom information. Therefore, burring along the proper X and Y plane, as well as the proper depth may be visually displayed with the appropriate indicia, as illustrated in FIG. 9. Rotational information about the corresponding X, Y and Z axes is also displayed. By burring within the safe zones 112 using the information regarding the surgical implant 52 as the safe zones 112, the surgeon can be assured to perform the proper burring between the vertebrae 200 and 202 to insure a proper oriented fit for the surgical implant 52. By tracking the burr 208 with six degrees of freedom information, the mounting anchors 212 for the hand piece 210 are optional and may not be required. Additionally, each single display in the dual display 10, as shown in FIG. 9, may also superimpose an image of each vertebrae 200 and 202 relative to one another on the display with each display having its coordinate system referenced to one of the vertebrae. The resulting milled vertebrae 200 and 202 are shown in FIG. 8e with a ring portion 214 milled to receive the spinal implant 52.

Referring to FIGS. 8f and 8g, the spinal implant 52 is shown being implanted between the vertebrae 200 and 202 using an implant inserter 216 that is also tracked by tracking sensor 58. By tracking the implant inserter 216 relative to the vertebrae 200 and 202, proper orientation of the spinal implant 52, as well as rotational orientation about the Z axis can be clearly displayed on the six degree of freedom display 10, as shown in FIG. 9. Rotation about the Z axis is used to make sure that the flanges 218 of the implant 52 are properly oriented and centered along the sagittal plane, as shown in FIG. 8g. Again, by using the display 10, as illustrated in FIG. 9, the anchors 220 are optional since orientation of the implant 52 can be tracked continuously as it is inserted between the vertebrae 200 and 202. Here again, this eliminates the need for forming holes in the vertebrae 200 and 202. It should further be noted that the implant 52 illustrated in these figures is merely an exemplary type of spinal implant and any known spinal implants may also be similarly tracked. For example, another common type of spinal implant is formed from a two-piece unit that includes a ball and cup articulating structure that may likewise be independently tracked to assure proper fit and placement.

Here again, the six degree of freedom display 10, which is illustrated as a split or dual display 10 in FIG. 9 assists a surgeon in implanting a spinal implant 52 in order to achieve proper fixation and orientation of the implant 52, relative to two movable vertebrae 200 and 202. By tracking each vertebra 200 and 202 independently, and tracking its resection, should one vertebra be resected off-plane due to anatomical anomalies, adjustment of the plane at the adjacent vertebra may be achieved in order to still provide a proper fit for the spinal implant 52. In this way, each vertebrae 200 and 202 can be independently monitored, so that if one is off axis, the other can be manipulated accordingly to account for this adjustment. Additionally, by monitoring the entire process having six degree of freedom information, via display 10, further accuracy was achieved, thereby providing increased range of motion for the patient after implantation of the implant 52.

By use of the six degree of freedom display, for the various types of medical procedures, improved results can be achieved by providing the surgeon with the necessary information required. In regard to surgical implants, the range of motion may be increased while reducing impingement of two-part articulating or fixed implants. This also enables maximum force transfer between the implant and the body. With therapy delivery procedures, by knowing the location of the catheter delivery tube and the specific port orientation, accurately aiming at the site is enabled to provide maximum delivery of the therapy at the correct site. This procedure also enhances and enables better results when using an ablation catheter by again knowing the rotational orientation of the ablation catheter and the ablation electrode relative to the area in the wall of the artery that requires ablation. Finally, by knowing the rotational orientation of a ablation or biopsy catheter, this type of catheter may be easily directed and aligned to tumors, stem cells, or other desired sites in an easy and efficient manner.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A navigation system for guiding a medical device to a target in a patient during a medical procedure, said navigation system comprising:

a display; and a workstation operably connected to the display and configured to process information from:

a tracking sensor associated with the medical device and operable to be used to track the medical device, and a tracking device operable to track the medical device with the tracking sensor to update a position of the medical device as the medical device is guided, the workstation, in response to the position of the medial device, configured to provide information for displaying on the display:

a first indicia identifying a first degree of freedom information;

a second indicia identifying a second degree of freedom information;

a third indicia identifying a third degree of freedom information;

a fourth indicia identifying a fourth degree of freedom information; and a fifth indicia identifying a fifth degree of freedom information;

a sixth indicia identifying a sixth degree of freedom information; and wherein said first, second, third, fourth, fifth and sixth indicia are illustrated on said display to assist in guiding the medical device to the target, the first, second, and third indicia are X, Y, and Z axes, respectively, with said X axis represented by a horizontal bar, said Y axis represented by a vertical bar crossing said X axis, and said Z axis represented by a separate bar, with a position of the medical device as the medical device is guided represented by an arrow on each of the displayed X axis, Y axis, and Z axis, and the fourth, fifth, and sixth indicia are rotation about the X, Y, and Z axes, respectively.

2. The navigation system as defined in claim 1 wherein the indicia are illustrated in a coordinate system selected from a group comprising a Cartesian coordinate system, a spherical coordinate system, a polar coordinate system, and a combination thereof.

3. The navigation system as defined in claim 1 wherein at least one of the indicia illustrates a safe zone in relation to said corresponding degree of freedom information.

4. The navigation system as defined in claim 3 wherein each indicia illustrates a safe zone.

5. The navigation system as defined in claim 3 wherein said safe zone is illustrated by way of color, audible tones, crosshatching and a combination thereof.

6. The navigation system as defined in claim 1 wherein the workstation further displays on the display an indicia of a tip portion of the medical device and an indicia of a hind portion of the medical device depicting the relative position and orientation of the medical device.

7. The navigation system as defined in claim 1 wherein rotation about the X axis is illustrated by a straight bar graph having an arrow identifying the amount of rotation, wherein the rotation about the Y axis is illustrated by a straight bar graph having an arrow illustrating the amount of rotation about the Y axis and the rotation about the Z axis is illustrated by an arcuate bar graph having an arrow illustrating the rotation about the Z axis.

8. The navigation system as defined in claim 1 wherein the workstation further displays on the display a target/trajectory indicia identifying the target/trajectory for the medical device.

9. The navigation system as defined in claim 8 wherein the workstation further displays on the display indicia of a second target/trajectory identifying a second target/trajectory.

10. The navigation system as defined in claim 8 wherein said target indicia is an origin.

11. The navigation system as defined in claim 1 wherein the workstation further displays on the display at least one of an image of the patient superimposed on said display and one of a model of the patient superimposed on said display.

12. The navigation system as defined in claim 1 wherein said display includes multiple displays.

13. The navigation system as defined in claim 1 wherein the workstation displays on the display said first, second, third, fourth and fifth indicia simultaneously.

14. The navigation system as defined in claim 1 wherein said display assists in the control of a surgical robot used during the medical procedure.

15. The navigation system as defined in claim 1 wherein the workstation further displays on the display a safe zone that is illustrated as a region of a first color on each of the bars different than a second color of the remaining portion of each bar.

16. The navigation system of claim 1, wherein the workstation further displays on the display a position of the instrument that is illustrated as an icon on a single display with the each of the bars and operable to be displayed separate from each of the bars.

17. The display navigation system of claim 1, wherein each of the degree of freedom information indicates a position of the instrument within a Cartesian coordinate system;
wherein the first degree of freedom information is a X axis position of the instrument, the second degree of freedom information is a Y axis position of the instrument, the third degree of freedom information is a Z axis position of the instrument, the fourth degree of freedom information is a rotation around the X axis of the instrument, the fifth degree of freedom information is a rotation around the Y axis of the instrument, and the sixth degree of freedom information is a rotation around the Z axis of the instrument.

18. The navigation system of claim 1, wherein the display includes a human viewable display having a width and a height;
wherein the X axis bar and the Y axis bar are positioned near a center of the display, the Z axis bar extends out from the display and is shown in an upper left corner, rotation about the X axis is shown by bar graph on a right of the display, rotation about the Y axis is shown by bar graph positioned at the bottom of the display, rotation about the Z axis is shown with an arcuate bar graph oriented about the X and Y axes.

19. A navigation system for use in guiding a medical device to a target in a patient during a medical procedure, said navigation system comprising:
a tracking sensor associated with the medical device and operable to be used to track the medical device;
a tracking device operable to track the medical device with the tracking sensor to update a position of the medical device as the medical device is guided; and
a workstation having a display, the workstation configured to provide information data for displaying on the display indicia illustrating at least five degrees of freedom information and indicia of the position of the medical device in relation to said at least five degrees of freedom information as the medical device is guided;
wherein the first, second, and third indicia are X, Y, and Z axes, respectively, with the X axis represented by a horizontal bar, the Y axis represented by a vertical bar crossing the X axis, and the Z axis represented by a separate bar, with the position of the medical device represented by an arrow on each of the displayed X axis, Y axis, and Z axis.

20. The navigation system as defined in claim 19 wherein said tracking sensor is attached to the medical device.

21. The navigation system as defined in claim 19 wherein said tracking sensor is selected from a group comprising an electromagnetic sensor, an optical sensor, an optical reflector, an electromagnetic transmitter, a conductive sensor, an acoustic sensor, or combinations thereof.

22. The navigation system as defined in claim 19 wherein said tracking device is selected from a group comprising an electromagnetic tracking device, an optical tracking device, a conductive tracking device, an acoustic tracking device, or combinations thereof.

23. The navigation system as defined in claim 19 further comprising an imaging device operable to generate image data of a region of the patient.

24. The navigation system as defined in claim 19 wherein said navigation system has an image-less based navigation system wherein said image-less navigation system is operable to generate a model representing a region of the patient.

25. The navigation system as defined in claim 19 further comprising a dynamic reference frame attached to the patient and operable to be used to track movement of the patient relative to said tracking device.

26. The navigation system as defined in claim 19 wherein the medical device is a medical instrument or implant.

27. The navigation system as defined in claim 19 wherein said indicia of the medical device includes indicia identifying a tip portion and indicia identifying a hind portion of the medical device.

28. The navigation system as defined in claim 27 wherein said tip includes indicia of crosshairs and said hind includes indicia of a circle.

29. The navigation system as defined in claim 19 wherein said medical device is a device having at least a first component and a second component where placement of said first component is dependent upon placement of said second component and wherein said display is operable to display proper position of said first component relative to said second component.

30. The navigation system as defined in claim 19, wherein at least three of the of the five degree of freedom information is illustrated on the display; and
   wherein a first degree of the five degree of freedom information includes the X axis represented by the horizontal axis bar and a second degree of the five degree of freedom information includes the Y axis represented by the vertical axis bar crossing the X axis bar, wherein a position of the medical device is illustrated by a cross-hair relative to the axis bars.

31. The navigation system as defined in claim 30, wherein rotation of the medical device about the X axis is illustrated by a straight bar graph having an arrow identifying the amount of rotation, wherein the rotation about the Y axis is illustrated by a straight bar graph having an arrow illustrating the amount of rotation about the Y axis, and the rotation about the Z axis is illustrated by an arcuate bar graph having an arrow illustrating the rotation about the Z axis.

32. The navigation system of claim 31, wherein the display includes a human viewable display having a width and a height;
   wherein the X axis bar and the Y axis bar are positioned near a center of the display, the Z axis bar extends out from the display and is shown in an upper left corner, rotation about the X axis is shown by bar graph on a right of the display, rotation about the Y axis is shown by bar graph positioned at the bottom of the display, rotation about the Z axis is shown with an arcuate bar graph oriented about the X and Y axes.

33. The navigation system of claim 19, wherein a position of the medical device is illustrated as an icon on a single display with the each of the bars and operable to be displayed separate from each of the bars.

34. The navigation system of claim 19, wherein each of the five degrees of freedom information indicates a position of the medical device within a Cartesian coordinate system;
   wherein three of the degrees of freedom include the first degree of freedom information is a X axis position of the medical device, the second degree of freedom information is a Y axis position of the medical device, the third degree of freedom information is a Z axis position of the medical device;
   wherein two of the degrees of freedom include at least two of the fourth degree of freedom information is a rotation around the X axis of the medical device, the fifth degree of freedom information is a rotation around the Y axis of the medical device, the sixth degree of freedom information is a rotation around the Z axis of the medical device, and combinations thereof.

35. A method for navigating and displaying a medical device during a medical procedure, said method comprising:
   selecting a target for navigating the medical device to;
   displaying the target in a coordinate system that includes an X axis represented by a horizontal bar, a Y axis represented by a vertical bar crossing the X axis, and a Z axis represented by a separate bar;
   tracking the medical device with a navigation system to determine a position of the medical device in the coordinate system; and
   displaying the medical device in relation to the target with at least five degrees of freedom information by displaying an indicia that indicates the position of the medical device on each of the X axis, Y axis and Z axis as the medical device is navigated.

36. The method as defined in claim 35 further comprising selecting a safe zone for at least one of the degrees of freedom information.

37. The method as defined in claim 36 further comprising selecting a safe zone for each degree of freedom information.

38. The method as defined in claim 35 further comprising aligning the medical device with the target using the five degree of freedom information.

39. The method as defined in claim 35 further comprising selecting a second target that is positioned in relation to the first target for a second medical device; and
   displaying the second target in the coordinate system.

40. The method as defined in claim 39 further comprising:
   tracking the second medical device; and
   displaying the second medical device in relation to the second target with the at least five degree of freedom information.

41. The method as defined in claim 40 further comprising aligning the second medical instrument with the second target.

42. The method as defined in claim 41 further comprising:
   determining whether the alignment of the first medical device and the second medical device are correct; and
   realigning the first medical device, the second medical device, or combinations thereof when the alignment is determined to be incorrect.

43. The method as defined in claim 35 wherein selecting the target further includes selecting a center of a joint.

44. The method as defined in claim 35 wherein selecting the target further includes selecting a target based upon an articulating plane of a joint.

45. The method as defined in claim 35 wherein selecting the target further includes selecting an area between a first vertebra and a second vertebra for placement of an implant.

46. The method as defined in claim 35 wherein selecting the target further includes selecting a site within an artery.

47. The method of claim 35, wherein displaying indicia includes:
   displaying the X axis as a first degree of the five degree of freedom information represented by the horizontal axis bar and a displaying the Y axis as a second degree of the five degree of freedom information represented by the vertical axis bar crossing the X axis bar, wherein a position of the medical device is illustrated by a cross-hair relative to the axis bars;
   displaying the Z axis as a third degree of the five degree of freedom information represented by the separate axis bar having an arrow identifying the position along the Z axis.

48. The method of claim 47, further comprising at least one of:
   displaying rotation of the medical device about the X axis by a straight bar graph having an arrow identifying the amount of rotation;
   displaying rotation of the medical device about the Y axis by a straight bar graph having an arrow illustrating the amount of rotation about the Y axis;
   displaying rotation of the medical device about the Z axis by an arcuate bar graph having an arrow illustrating the rotation about the Z axis;
   or combinations thereof.

49. The method of claim 47, wherein a position of the medical device is represented by an arrow relative to each of the displayed X axis bar, Y axis bar, and Z axis bar.

50. The method of claim 47, wherein a position of the medial device is illustrated as an icon on a single display with the each of the bars and operable to be displayed separate from each of the bars.

51. The display of claim 47, further comprising:
- providing a human viewable display having a width and a height;
- positioning the X axis bar and the Y axis bar near a center of the display
- positioning the Z axis bar as extending out from the display and in an upper left corner of the display;
- positioning a bar graph illustrating rotation about the X axis on a right of the display;
- positioning a bar graph illustrating rotation about the Y axis at the bottom of the display; and
- positioning an arcuate bar graph illustrating rotation about the Z axis oriented about the X axis and Y axis bars.

52. The display of claim 35, wherein each of the five degrees of freedom information indicates a position of the medical device within a Cartesian coordinate system;
- wherein three of the degrees of freedom include the first degree of freedom information is a X axis position of the medical device, the second degree of freedom information is a Y axis position of the medical device, and the third degree of freedom information is a Z axis position of the medical device;
- wherein two of the degrees of freedom include at least two of the fourth degree of freedom information is a rotation around the X axis of the medical device, the fifth degree of freedom information is a rotation around the Y axis of the medical device, the sixth degree of freedom information is a rotation around the Z axis of the medical device, or combinations thereof.

* * * * *

UNITED STATES PATENT AND TRADEMARK OFFICE
CERTIFICATE OF CORRECTION

| | | |
|---|---|---|
| PATENT NO. | : 7,660,623 B2 | Page 1 of 1 |
| APPLICATION NO. | : 10/354562 | |
| DATED | : February 9, 2010 | |
| INVENTOR(S) | : Hunter et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1439 days.

Signed and Sealed this

Thirtieth Day of November, 2010

David J. Kappos
*Director of the United States Patent and Trademark Office*